(12) United States Patent
Yu et al.

(10) Patent No.: US 10,744,227 B2
(45) Date of Patent: *Aug. 18, 2020

(54) CO-CROSSLINKED HYALURONIC ACID-SILK FIBROIN HYDROGELS FOR IMPROVING TISSUE GRAFT VIABILITY AND FOR SOFT TISSUE AUGMENTATION

(71) Applicant: Allergan, Inc., Irvine, CA (US)

(72) Inventors: Xiaojie Yu, Orange, CA (US); Darin J. Messina, Laguna Niguel, CA (US); Elizabeta Pavlovic, Los Angeles, CA (US); Cunqi Cui, Jurupa Valley, CA (US); Kate M. Smither, Newbury Park, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/400,995

(22) Filed: May 1, 2019

(65) Prior Publication Data

US 2019/0255215 A1 Aug. 22, 2019

Related U.S. Application Data

(62) Division of application No. 15/686,036, filed on Aug. 24, 2017, now Pat. No. 10,300,169.

(60) Provisional application No. 62/379,045, filed on Aug. 24, 2016.

(51) Int. Cl.
*A61L 27/20* (2006.01)
*C08H 1/00* (2006.01)
*A61L 27/18* (2006.01)
*C08B 37/08* (2006.01)
*A61F 2/52* (2006.01)

(52) U.S. Cl.
CPC ............... *A61L 27/20* (2013.01); *A61L 27/18* (2013.01); *C08B 37/0072* (2013.01); *C08H 1/00* (2013.01); *A61F 2/52* (2013.01); *A61L 2400/06* (2013.01); *A61L 2430/34* (2013.01)

(58) Field of Classification Search
CPC .. A61L 27/20; A61L 2400/06; A61L 2430/04; A61L 2430/34; A61L 27/227; A61L 27/3604; A61L 27/52; C08L 5/08; C08L 89/00; A61K 8/64; A61K 8/735; A61Q 19/08

See application file for complete search history.

(56) References Cited

U.S. PATENT DOCUMENTS

| | | | |
|---|---|---|---|
| 5,017,229 A | 5/1991 | Burns et al. | |
| 6,610,669 B1 | 8/2003 | Calais et al. | |
| 6,903,199 B2 | 6/2005 | Moon et al. | |
| 9,149,422 B2 | 10/2015 | Liu et al. | |
| 9,393,263 B2 | 7/2016 | Liu et al. | |
| 9,408,797 B2 | 8/2016 | Njikang et al. | |
| 9,737,633 B2 | 8/2017 | Liu et al. | |
| 9,950,092 B2 | 4/2018 | Njikang et al. | |
| 9,962,464 B2 | 5/2018 | Liu et al. | |
| 10,300,169 B2 * | 5/2019 | Yu | A61L 27/18 |
| 2001/0039336 A1 | 11/2001 | Miller et al. | |
| 2003/0096879 A1 | 5/2003 | Fratini et al. | |
| 2007/0196426 A1 | 8/2007 | Hermitte et al. | |
| 2008/0004421 A1 | 1/2008 | Chenault et al. | |
| 2009/0017091 A1 | 1/2009 | Daniloff et al. | |
| 2009/0143331 A1 | 6/2009 | Stroumpolis et al. | |
| 2009/0263447 A1 | 10/2009 | Asius et al. | |
| 2010/0016886 A1 | 1/2010 | Lu | |
| 2010/0316683 A1 | 12/2010 | Piron et al. | |
| 2011/0171286 A1 | 7/2011 | Cecile et al. | |
| 2011/0171311 A1 | 7/2011 | Gousse et al. | |
| 2012/0301436 A1 | 11/2012 | Yang et al. | |
| 2013/0096081 A1 | 4/2013 | Njikang et al. | |
| 2013/0236429 A1 | 9/2013 | Melero-Martin | |
| 2014/0315828 A1 | 10/2014 | Pavlovic et al. | |
| 2015/0064147 A1 | 3/2015 | Pollock et al. | |
| 2016/0113855 A1 | 4/2016 | Njikang | |
| 2017/0136145 A1 | 5/2017 | Liu et al. | |

FOREIGN PATENT DOCUMENTS

| | | |
|---|---|---|
| CN | 102836465 | 12/2012 |
| EP | 1115433 | 12/2004 |
| EP | 1932530 | 6/2008 |
| FR | 2873379 | 7/2004 |
| JP | 2009-508991 | 3/2009 |
| JP | 2009-528438 | 8/2009 |
| JP | 2010-509425 | 3/2010 |
| WO | WO 01/058961 | 8/2001 |

(Continued)

OTHER PUBLICATIONS

"Belotero—It's a part of me," Merz Aesthetics, May 2014, retrieved from https://aadfa.net/media/resources_forms/Belotero_product_catalogue.pdf, 36 pages.

Berezovsky, "Oxygen tension in blood with hypoxia and adaptation to oxygen deficit," (Ukranian) Fiziologicheskii Zhurnal, 1973, 800-805, vol. 19, Issue 6.

Brandt et al., "Hyaluronic Acid Gel Fillers in the Management of Facial Aging," Clinical Interventions in Aging, 2008, 153-159, 3(1).

Database WPI, Week 201140, Thomson Scientific, London, GB, AN2011-G55502 & WO 2011/068303 A2 (Cellinbio Co Ltd) Jun. 9, 2011 (Jun. 9, 2011).

Huang et al., "New Adipose Tissue Formation by Human Adipose-Derived Stem Cells with Hyaluronic Acid Gel in Immunodeficient Mice," International Journal of Medical Sciences, Jan. 2015, vol. 12, pp. 154-162.

(Continued)

*Primary Examiner* — Audrea B Coniglio
*Assistant Examiner* — Audrea Buckley
(74) *Attorney, Agent, or Firm* — Nathan S. Smith; Richard W. Martin; Morgan, Lewis & Bockius LLP

(57) ABSTRACT

Hydrogels comprising a macromolecular matrix and water may be used to augment soft tissue of a human being, promote or support cell or tissue viability or proliferation, create space in tissue, and for other purposes. A macromolecular matrix may comprise a hyaluronic acid component crosslinked to a silk fibroin component.

26 Claims, 3 Drawing Sheets

(56) References Cited

FOREIGN PATENT DOCUMENTS

| WO | WO 2004/067575 | 8/2004 |
|---|---|---|
| WO | WO 2007/127277 | 12/2007 |
| WO | WO 2009/018076 | 2/2009 |
| WO | WO 2009/073437 | 6/2009 |
| WO | WO 2010/029344 | 3/2010 |
| WO | WO 2010/123945 | 10/2010 |
| WO | WO 2011/023355 | 10/2011 |
| WO | WO 2012/167079 | 12/2012 |
| WO | WO 2013/040242 | 3/2013 |
| WO | WO 2017/031169 | 2/2017 |

OTHER PUBLICATIONS

International Search Report and Written Opinion from PCT/2017/048495, dated Nov. 2, 2017, 9 pages.

Jeon et al., "Mechanical Properties and Degradation Behaviors of Hyaluronic Acid Hydrogels Cross-Linked at Carious Cross-Linked Densities," Carbohydrate Polymers, 2007, 251-257, 70.

Meves et al., "Vitamin C Derivative Ascorbyl Palmitate Promotes Ultraviolet-B-Induced Lipid Peroxidation and Cytotoxicity in Keratinocytes," The Journal of Investigative Dermatology, Nov. 2002, 1103-1108, vol. 119, No. 5.

Murphy et al., "Biomedical applications of chemically-modified silk fibroin," Journal of Materials Chemistry, 2009, 19, 6443-6450.

Park et al., "In Vitro Evaluation of Conjugated Hyaluronic Acid With Ascorbic Acid," Journal of Bone and Joint Surgery, 2010, 115 92.

Tomihata et al., "Crosslinking of Hyaluronic Acid with Water-Soluable Carbodiimide," J Biomed Mater Res, Feb. 1997, 243-251, vol. 37(2).

Yeom et al., "Effect of Cross-Linking Reagents for Hyaluronic Acid Hydrogel Dermal Fillers on Tissue Augmentation and Regeneration," Bioconjugate Chem, 2010.

Zhu et al., "Manual Isolation of Adipose-derived Stem Cells from Human Lipoaspirates," J. Vis. Exp. (79) e50585, Sep. 2013, 10 pages.

\* cited by examiner (Lipo Only)

(Lipo Only)

(Lipo + HA-Fbn 19:2)

(Lipo + HA-Fbn 19:2)

(Lipo + HA-Fbn 18:3)

(Lipo + HA-Fbn 17:4)

(Lipo + HA-Fbn 18:3)

(Lipo + HA-Fbn 17:4)

CO-CROSSLINKED HYALURONIC ACID-SILK FIBROIN HYDROGELS FOR IMPROVING TISSUE GRAFT VIABILITY AND FOR SOFT TISSUE AUGMENTATION

CROSS-REFERENCE TO RELATED APPLICATIONS

This application is a divisional of U.S. patent application Ser. No. 15/686,036, filed on Aug. 24, 2017, which claims priority to and the benefit of U.S. Provisional Patent Application Ser. No. 62/379,045, filed Aug. 24, 2016, each of which is incorporated herein by reference in their entirety.

BACKGROUND

Field of the Inventions

The present disclosure generally relates to crosslinked silk-hyaluronic acid compositions, methods of making and uses thereof, and more specifically relates to silk-hyaluronic acid compositions useful for improving tissue graft viability and soft tissue augmentation.

Description of the Related Art

Autologous fat transfer ("AFT"), also known as fat grafting, is a process by which fat is harvested from one part of a human body and injected into another part of the same person's body where additional bulk may be needed for cosmetic and/or aesthetic purposes. Clinical applications for autologous fat transfer are expanding rapidly with recent reported use in breast reconstruction and augmentation, buttock enhancement, treatment of congenital tissue defects, facial reconstruction, and skin rejuvenation. Although this is a very attractive approach and there is an increased trend in replacement of soft tissue volume with AFT, typical survival rates of grafted fat may be poor and overall results may not be satisfactory to a patient.

AFT has been shown to be enhanced by the inclusion of hydrogels or other scaffolds for tissue engineering. U.S. Pat. No. 9,662,422 to Pollock et al.; Crosslinked hyaluronic acid-collagen gels for improving tissue graft viability and soft tissue augmentation; describes the use of a hyaluronic acid-collagen hydrogel in AFT. U.S. Patent Application Pub. No. 2013/0244943 A1: Yu et al.; Hyaluronic acid-collagen matrices for dermal filling and volumizing applications; describes the production of cross-linked hyaluronic acid and collagen compositions. U.S. Pat. No. 9,408,797 to Nijkang et al.; Dermal filler compositions for fine line treatment; describes the use of a dermal filler comprising hyaluronic acid crosslinked with collagen in the treatment of facial wrinkles. Each of these references is herein incorporated by reference in their entirities.

Hyaluronic acid (HA) (synonymously "hyaluron" or "hyaluronate") is a naturally occurring glycosaminoglycan that has been used as a constituent of a dermal filler for wrinkle reduction and tissue volumizing. Hyaluronan is an anionic, nonsulfated glycosaminoglycan distributed widely throughout connective, epithelial, and neural tissues. Polymeric hyaluronic acid can have a molecular weight of several million Daltons. A person typically has about 15 grams of hyaluronan in his body about a third of which every day is degraded by endogenous enzymes and free radicals within a few hours or days and replaced by hyaluronic acid newly synthesized by the body.

Silk is a natural (non-synthetic) protein made of high strength fibroin fibers with mechanical properties similar to or better than many of synthetic high performance fibers. Silk is also stable at physiological temperatures in a wide range of pH, and is insoluble in most aqueous and organic solvents. As a protein, unlike the case with most if not all synthetic polymers, the degradation products (e.g., peptides, amino acids) of silk are biocompatible. Silk is non-mammalian derived and carries far less bioburden than other comparable natural biomaterials (e.g., bovine or porcine derived collagen). Silk, as the term is generally known in the art, means a filamentous fiber product secreted by an organism such as a silkworm or spider. Silks can be made by certain insects such as for example *Bombyx mori* silkworms, and *Nephila clavipes* spiders. There are many variants of natural silk. Fibroin is produced and secreted by a silkworm's two silk glands. As fibroin leaves the glands it is coated with sericin a glue-like substance. Spider silk is produced as a single filament lacking the immunogenic protein sericin.

Silk has been used in biomedical applications. The *Bombyx mori* species of silkworm produces a silk fiber (a "bave") and uses the fiber to build its cocoon. The bave as produced include two fibroin filaments or broins, which are surrounded with a coating of the gummy, antigenic protein sericin. Silk fibers harvested for making textiles, sutures and clothing are not sericin extracted or are sericin depleted or only to a minor extent and typically the silk remains at least 10% to 26% by weight sericin. Retaining the sericin coating protects the frail fibroin filaments from fraying during textile manufacture. Hence textile grade silk is generally made of sericin coated silk fibroin fibers. Medical grade silkworm silk is used as either as virgin silk suture, where the sericin has not been removed, or as a silk suture from which the sericin has been removed and replaced with a wax or silicone coating to provide a barrier between the silk fibroin and the body tissue and cells. Thus there is a need for a sericin extracted implantable, bioresorbable silk device that promotes ingrowth of cells.

Bioconjugate Chemistry, 2010, 21, 240-247: Joem Y., et al., *Effect of cross-linking reagents for hyaluronic acid hydrogel dermal fillers on tissue augmentation and regeneration*, discusses use of a particular cross-linked HMDA to prepare a cross-linked hyaluronic acid dermal filler, and also discloses use of a variety of hyaluronic acid cross linkers and hyaluronic activators including BDDE and EDC. Carbohydrate Polymers, 2007, 70, 251-257: Jeon, O., et al., *Mechanical properties and degradation behaviors of hyaluronic acid hydrogels cross-linked at various cross-linking densities*, discusses properties of hyaluronic acid cross linked with a polyethylene glycol diamine (a PEG-diamine). J. Am. Chem. Soc., 1955, 77 (14), 3908-3913: Schroeder W., et al., *The amino acid composition of Bombyx mori silk fibroin and of Tussah silk fibroin*, compares the amino acid compositions of the silk from two silkworm species. U.S. Patent Application Pub. No. US 2010/0016886 A1: Lu, H., High swell, long lived hydrogel sealant; discusses reacting a multi-arm amine (i.e., an 9 arm polyethelene glycol (PEG) with an oxidized (i.e., to introduce aldehyde groups) polysaccharide (such as hyaluronic acid), useful for tissue augmentation or a tissue adhesive/sealant. U.S. Pat. No. 6,903,199 to Moon. T., et al., Crosslinked amide derivatives of hyaluronic acid and manufacturing method thereof discusses cross linking hyaluronic acid with a chitosan or with a deacetylated hyaluronic acid with reactive amide groups, using (for example) EDC or NHS. U.S. Patent Application Pub. No. US 2016/0361247 A1:

Pavlovic et al., Cross linked silk-hyaluronic acid composition; describes methods for cross-linking silk with hyaluronic acid. U.S. Pat. No. 8,288,347 to Collette et al., Dermal fillers comprising silk fibroin hydrogels and uses thereof describes methods for purifying silk fibroins and hydrogels comprising silk fibroin with or without an amphiphilic peptide.

International Patent Application WO/2010/123945, Altman, G., et al., Silk fibroin hydrogels and uses thereof discusses silk hydrogels made by, for example, digesting degummed silk hydrogels made by, for example, digesting degummed *Bombyx mori* silk at 60° C. for 4 hours in 9.3M lithium bromide to thereby obtain a 20% silk solution, an 8% silk solution of which was induced to gel using 23RGD and/or ethanol, which can be present in a hyaluronic acid carrier. Altman also discusses possible use as a dermal filler and to promote wound closure, and a silk hydrogel coating on a silk mesh. Altman also discusses silk cross linked to hyaluronic acid (see paragraphs [213] to [220], using various cross linkers.

International Patent Application. Pub. No. WO/2008/008857: Prestwich, G., et al., Tholated macromolecules and methods for making and using thereof discloses a thioethyl ether substituted hyaluronic acid made by oxidating coupling useful, for example, in arthritis treatment. International Patent Application. Pub. No. WO/2008/008859: Prestwich, G., et al., Macromolecules modified with electrophilic groups and methods of making and using thereof discloses a haloacetate derivative hyaluronic acid reacted with thiol modified hyaluronic acid to make a hydrogel, with various medical uses. Biomacromolecules, 2010, 11 (9), 2230-2237: Serban, M., et. Al., *Modular elastic patches: mechanical and biological effects* discusses how to make an elastic patch by cross linking elastin, hyaluronic acid and silk, by adding an aminated hyaluronic acid (made using EDC) with a 20% silk solution and elastin, in phosphate buffered saline (PBS) with BS3 (bissulfosuccinimidyl suberate, as cross linker) at 37° C. for 12 hours. Biomaterials, 2008, 29(10), 1388-1399: Serban, M., et al., *Synthesis, characterization and chondroprotective properties of a hyaluronan thioethyl ether derivative* discusses a viscous 2-thioethyl ether hyaluronic acid derivative solution useful for viscosupplementation in arthritis treatment. The abstract mentions that a prior hyaluronic acid with multiple thio groups can be used for adhesion prevention. Methods, 2008, 45, 93-98: Serban, M., et al., *Modular extracellular matrices: solutions to the puzzle* discusses cross linked thio modified hyaluronic acid hydrogel useful as a semi synthetic extracellular matrix for cell culture. Biomacromolecules, 2007, 8(9), 2821-2828: Serban, M., et al., *Synthesis of hyaluronan haloacetates and biology of novel cross linker free synthetic extracellular matrix hydrogels* discusses cross linking haloacetate substituted hyaluronic acids reacted with a thiol substituted hyaluronic acid to make a hydrogel useful for cell culture or adhesion prevention or medical device coating. Journal of Materials Chemistry, 2009, 19, 6443-6450: Murphy A., et al., *Biomedical applications of chemically modified silk fibroin* is a review of methods to make silk conjugates, including silk conjugated to oligosaccharides, modified silk and medical uses. Biomacromolecules, 2004, 5, 751-757: Sohn, S., et al., *Phase behavior and hydration of silk fibroin* discusses a study of *Bombyx mori* silk in vitro using osmotic stress, determining that silk I ($\alpha$-silk) but not silk II ($\beta$-sheet, spun silk fiber) is hydrated. U.S. Pat. No. 8,071,722 to Kaplan, D., et al., Silk Biomaterials and methods of use thereof discloses silk films, use of 9-12 m LiBr to dissolve extracted silk, adding hyaluronic acid to a silk solution to make fibers from the composition. See also eg the Kaplan patents and application U.S. Pat. Nos. 7,674,882; 8,178,656; 2010 055438, and; 2011 223153. U.S. Patent application 2011 071239 by Kaplan, D., et al., PH induced silk gels and uses thereof discloses methods for making silk fibroin gel from silk fibroin solution, useful to coat a medical device using implants, as an injectable gel to fill a tissue void, making an adhesive silk gel (with or without a hyaluronic acid), adhering the adhesive silk gel to a subject for example for use as a wound bioadhesive, a multi-layered silk gel. U.S. Patent application 2009 0202614 by Kaplan, D., et al., Methods for stepwise deposition of silk fibroin coatings discusses layered silk coatings, silk films made using silk fibroin solutions, which can include a hyaluronic acid, useful, for example, as wound healing patches, to coat an implantable medical device. U.S. Pat. No. 4,818,291 to Iwatsuki M., et al., Silk-fibroin and human-fibrinogen adhesive composition discusses surgical adhesive useful in tissue repair made as a mixture of LiBr dissolved silk and fibrinogen.

To increase in vivo residence time, the linear chains of hyaluronic acid can be crosslinked with a small molecular cross linker such as, for example, butanediol diglycidyl ether (BDDE) or 1-ethyl-3-[3-dimethylaminopropyl]carbodiimide hydrochloride (EDC) chemistry. Crosslinking hyaluronic acid with BDDE is usually carried out at high pH (>12) and at temperatures of about 50° C. It has been reported that the degradation rate constant of HA is increased roughly 100 times when the temperature and pH are both increased from 40 to 60° C. and 7 to 11 respectively.

SUMMARY

The present disclosure addresses these and other shortcomings in the field of cosmetic and reconstructive medicine and procedures.

Hydrogels and hydrogel compositions have been developed that are useful for soft tissue augmentation procedures, including tissue reconstruction procedures. These hydrogels and hydrogel compositions may promote and/or support the survival or growth of living cells and other components of tissues.

In some embodiments, a soft tissue augmentation product is provided, which can be injected or introduced into tissue along with a cellular component. The product may comprise a forming component comprising a hydrogel described herein, the hydrogel having a form suitable for augmenting human soft tissue by introducing, for example, by injection or implantation, the forming component into the human tissue. In some embodiments, the hydrogel itself contains or includes a cellular material, for example, living tissue or living cells, and a component hyaluronic acid and silk fibroin. The product may further comprise a label including instructions for such injecting or implanting the forming component. In addition, the product may, in some embodiments, include a syringe or other device for facilitating the introducing of the forming component.

Typically, in accordance with some embodiments, a hydrogel or a hydrogel composition may comprise water, and a crosslinked macromolecular matrix. The matrix may be in a form suitable for mixing or combining with living cells or tissue prior to introduction of the matrix into the portion or anatomical feature being augmented. In some embodiments, the matrix comprises a hyaluronic acid component; and a silk fibroin component. In some embodiments, the hyaluronic acid is crosslinked to the silk fibroin, for example, by a crosslinking component. In one especially advantageous embodiment, at least a portion of the crosslink units of the crosslinking component comprises an ester bond or an amide bond.

In some embodiments, methods of augmenting soft tissue of a human being are provided, which comprise injecting or implanting a hydrogel composition described herein into a soft tissue of the human being to thereby augment the soft tissue. In some embodiments, the method includes combining, or mixing the hydrogel composition with living cells or tissue that have been explanted from the patient. The composition may be especially effective in enhancing cell proliferation and/or supporting cell viability when reintroduced, for example, into a breast of a patient. Thus, the method in these instances may be useful in conjunction with fat grafting procedures.

Some embodiments are directed toward methods of promoting or supporting cell proliferation or survival, for example, in fat grafting procedures or other augmentation or reconstructive procedures. For example, the methods may include contacting hydrogel compositions described herein with cellular materials, cells and/or tissue, for example, prior to injecting the compositions into the body.

In some embodiments, methods are provides for preparing a space in human or animal tissue, for example, for later receipt of a fat graft or implant, the method comprising injecting a hydrogel composition described herein into the tissue, and allowing growth or proliferation of tissue while the composition degrades over time.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
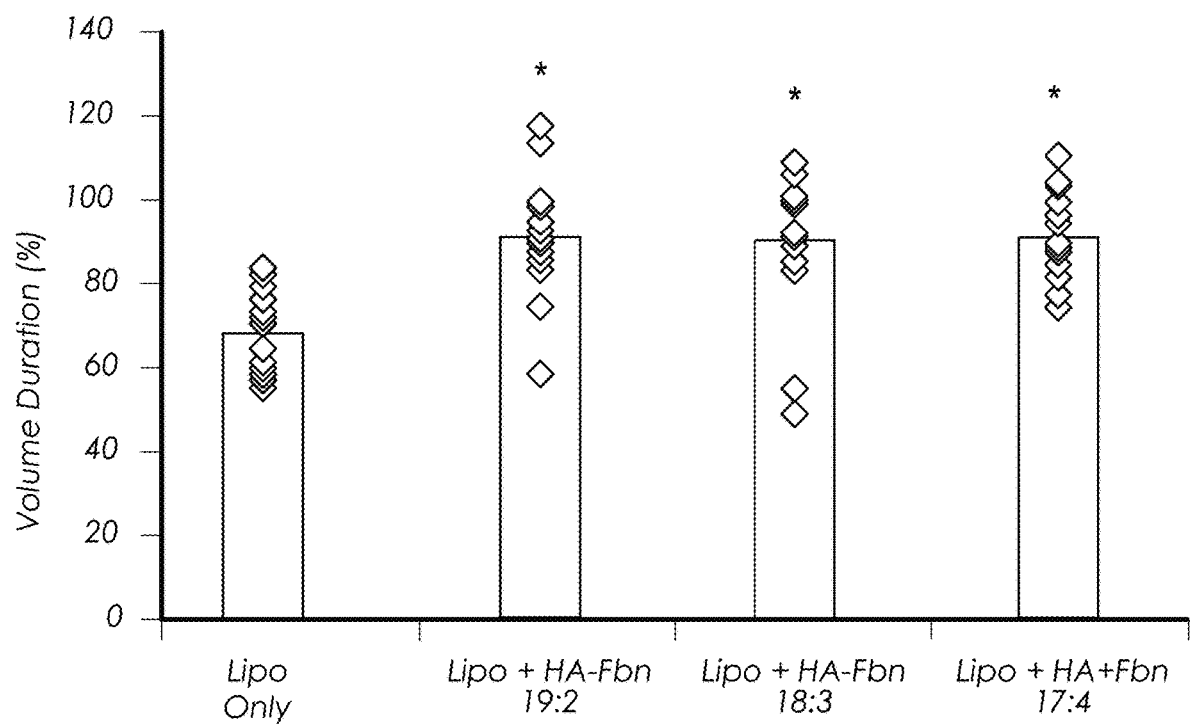
FIG. 1 provides a graph showing the in vivo volume retention over time for hyalruonic acid-silk fibroin (HA-Fbn) hydrogels combined with lipoaspirate in comparison with a lipoaspirate-only control.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Hydrogels described herein may be used to augment soft tissue of a human being. For example, a hydrogel or a hydrogel composition may be injected or implanted a hydrogel composition into a soft tissue of the human being to thereby augment the soft tissue. In some embodiments, a forming component may comprise a hydrogel or a hydrogel having a form suitable for augmenting human soft tissue by injecting or implanting the forming component into the human tissue.

A forming component may be any object or substance with a form that is suitable for a particular augmentation need. For example, a forming component may have a viscosity, firmness, and/or other physical properties, such that, when injected or implanted into a soft tissue to augment the tissue, the newly augmented portion of the tissue is reasonably similar to the natural tissue. If a forming component is to be injected, it may be in a form that is suitable for injection. For example, the viscosity may be low enough so that injection through a needle is possible. If a forming component is to be implanted, in some circumstances it may be desirable for the forming component to be solid or sufficiently viscous so as to maintain its shape during implantation.

Some augmentation products may include a label comprising instructions to inject or implant the forming component into the human tissue.

Hydrogels described herein may also be used to enhance, promote or support cell proliferation or survival. Some embodiments include a method comprising contacting a hydrogel or a hydrogel composition with a cell or cells.

A hydrogel or a hydrogel composition that contacts one or more cells may promote or support survival of the cells, including adypocytes, adipose-derived stem cells, stromal vascular fraction cells, or a combination thereof. For example, a hydrogel or a hydrogel composition described herein may promote or support cell survival to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition described herein may promote or support cell survival to a greater extent than a hydrogel composition comprising water and hyaluronic acid at a concentration of about 24 mg/mL or about 16 mg/mL. Contact between a hydrogel or a hydrogel composition described herein and cells may promote or support cell survival in vivo to a greater extent than a hydrogel composition that is substantially identical except that the hyaluronic acid component and the silk fibroin component are not crosslinked. In some embodiments, a hydrogel or a hydrogel composition may promote or support cell survival about as well as, or better than, tissue culture polystyrene.

A hydrogel composition disclosed herein may enhance survival of one or more cells. In one embodiment, a hydrogel composition disclosed herein enhances survival of one or more cells as compared to cells alone. In some embodiments, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells alone. In some embodiments, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500%, as compared to cells alone.

In some embodiments, a hydrogel composition disclosed herein enhances survival of one or more cells as compared to cells with a hydrogel composition that is substantially identical except that the hyaluronic acid component and the silk fibroin component are not crosslinked. In some embodiments, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the hyaluronic acid component and the silk fibroin component are not crosslinked. In some embodiments, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL and water.

In yet another embodiment, a hydrogel composition disclosed herein enhances survival of one or more cells as compared to cells with a hydrogel composition that is substantially identical except that the silk fibroin component is absent. In some embodiments, a hydrogel composition disclosed herein enhances survival of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the silk fibroin component is absent. In some embodiments, a hydrogel composition disclosed herein enhances survival of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL and water.

A hydrogel or a hydrogel composition that contacts one or more cells may promote or support proliferation of cells, such as regenerative cells, stem cells, progenitor cells, precursor cells, adipose-derived stem cells, stromal vascular fraction cells, etc. A hydrogel or a hydrogel composition described herein may also promote or support cell proliferation to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition described herein may promote or support cell proliferation to a greater extent than a hydrogel composition comprising water and hyaluronic acid at a concentration of about 24 mg/mL or about 16 mg/mL. Contact between a hydrogel or a hydrogel composition described herein and cells may promote or support cell proliferation to a greater extent than a hydrogel composition that is substantially identical except that the hyaluronic acid component and the silk fibroin component are not crosslinked. In some embodiments, a hydrogel or a hydrogel composition may promote or support cell proliferation about as well as, or better than, tissue culture polystyrene.

A hydrogel composition disclosed herein may enhance proliferation of one or more cells. In one embodiment, a hydrogel composition disclosed herein enhances proliferation of one or more cells as compared to cells alone. In some embodiments, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500 as compared to cells alone. In some embodiments, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500%, as compared to cells alone.

In another embodiment, a hydrogel composition disclosed herein enhances proliferation of one or more cells as compared to cells with a hydrogel composition that is substantially identical except that the hyaluronic acid component and the silk fibroin component are not crosslinked. In some embodiments, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the hyaluronic acid component and the silk fibroin component are not crosslinked. In some embodiments, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In yet another embodiment, a hydrogel composition disclosed herein enhances proliferation of one or more cells as compared to cells with a hydrogel composition that is substantially identical except that the silk fibroin component is absent. In some embodiments, a hydrogel composition disclosed herein enhances proliferation of one or more cells by at least about 50% at least about 100%, at least about 150%, at least about 200%, at least 250%, at least about 300%, at least about 350%, at least about 400%, at least about 450%, or at least about 500% as compared to cells with a hydrogel composition that is substantially identical except that the silk fibroin component is absent. In some embodiments, a hydrogel composition disclosed herein enhances proliferation of one or more cells by about 50% to about 250%, about 50% to about 500%, about 50% to about 1000%, about 100% to about 300%, about 100% to about 500%, about 150% to about 400%, about 150% to about 500%, or about 200% to about 500% as compared to cells with a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

A hydrogel or a hydrogel composition of the present disclosure may include a cellular component, for example, components of human adipose tissue, for example, adipose-derived stem cells, stromal vascular fraction cells, etc.

When injected or implanted in vivo, a hydrogel or a hydrogel composition may promote cell and/or tissue growth, including growth into the implant material. For example, a hydrogel or hydrogel composition may stimulate angiogenesis, neovascularization, adipogenesis, collagenesis, cell infiltration, tissue integration, and the like in vivo. In some embodiments, a hydrogel or a hydrogel composition may promote this type of growth or activity to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition may promote this type of growth or activity to a greater extent than a hydrogel composition comprising water and hyaluronic acid at a concentration of about 24 mg/mL or about 16 mg/mL. In some embodiments, a hydrogel or a hydrogel composition may promote this type of growth or activity to a greater extent than a hydrogel composition that is substantially identical except that the hyaluronic acid component and the silk fibroin component are not crosslinked Once injected or implanted into a soft tissue, a hydrogel composition disclosed herein may stimulate angiogenesis, neovascularization, adipogenesis, and/or collagenesis. In an embodiment, a hydrogel composition disclosed herein stimulates angiogenesis, neovascularization, adipogenesis, and/or collagenesis to a greater extent as compared to a hydrogel composition that is substantially identical except that the hyaluronic acid component and the silk fibroin component are not crosslinked. In some embodiments, a hydrogel composition disclosed herein angiogenesis, neovascularization, adipogenesis, and/or collagenesis by at least about 50% at least about 100%, at least about 150%, at least about 200%, at least 250%, at least about 300%, at least about 350%, at least about 400%, at least about 450%, at least about 500%, at least about 750%, or at least about 1000% as compared to a hydrogel composition that is substantially identical except that the hyaluronic acid component and the silk fibroin component are not crosslinked. In some embodiments, a hydrogel composition disclosed herein angiogenesis, neovascularization, adipogenesis, and/or collagenesis by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein stimulates angiogenesis, neovascularization, adipogenesis, and/or collagenesis to a greater extent as compared to adipose tissue with a hydrogel composition that is substantially identical except that the silk fibroin component is absent. In some embodiments, a hydrogel composition disclosed herein angiogenesis, neovascularization, adipogenesis, and/or collagenesis by at least about 50% at least about 100%, at least about 150%, at least about 200%, at least 250%, at least about 300%, at least about 350%, at least about 400%, at least about 450%, at least about 500%, at least about 750%, or at least about 1000% as compared to a hydrogel composition that is substantially identical except that the silk fibroin component is absent. In some embodiments, a hydrogel composition disclosed herein angiogenesis, neovascularization, adipogenesis, and/or collagenesis by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

Once injected or implanted into a soft tissue, a hydrogel composition disclosed herein may show infiltration and/or tissue integration of cells from the soft tissue. In an embodiment, a hydrogel composition disclosed herein shows cell infiltration and/or tissue integration from the soft tissue to a greater extent as compared to a hydrogel composition that is substantially identical except that the hyaluronic acid component and the silk fibroin component are not crosslinked. In some embodiments, a hydrogel composition disclosed herein shows enhanced cell infiltration and/or tissue integration by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the silk fibroin component are not crosslinked. In some embodiments, a hydrogel composition disclosed herein shows enhanced cell infiltration and/or tissue integration by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein may show cell infiltration and/or tissue integration from the soft tissue to a greater extent as compared to a hydrogel composition that is substantially identical except that the silk fibroin component is absent. In some embodiments, a hydrogel composition disclosed herein shows enhanced cell infiltration and/or tissue integration by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the silk fibroin component is absent. In some embodiments, a hydrogel composition disclosed herein shows enhanced cell infiltration and/or tissue integration by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

In some methods, hydrogel or a hydrogel composition may be mixed with tissue, for example, adipose tissue or fat tissue from the human being, such as human lipoaspirate, or from fat from another human being or an animal. The tissue may comprise adipose-derived progenitor cells, for example, adipose-derived stem cells. In some embodiments, methods are provided for soft tissue augmentations and fat grafting using such cell and filler compositions, which include autologous cells, for example, autologous, adipose-derived adult stem and/or progenitor cells. The ratio of hydrogel to fat in such a mixture may vary to provide the desired results. The fat:hydrogel ratio is the weight of the fat divided by the weight of hydrogel. For example, if 1 gram of fat is mixed with 10 grams of hydrogel, the fat:hydrogel weight ratio is 0.1. In some embodiments, the fat tissue and the hydrogel may have a fat:hydrogel weight ratio of about 0.1 up to about 10. All other fat:hydrogel weight ratios falling within this range are also contemplated and considered to be within the scope of some embodiments. For example, the weight ratio may be about 0.5 up to about 7, for example, about 1 up to about 5. In some embodiments, the fat:hydrogel weight ratio is about 1 to about 3, for example, about 1, about 2, or about 3.

A combination or mixture of human fat tissue and hydrogel composition may then be injected or implanted into soft tissue of a human being, for augmenting the breast for example. This may help to improve the survival time of grafted fat in autologous and other fat transfer procedures. It may also help to improve volume retention, reduce the variability in retained fat graft volume, and/or reduce inflammation as compared to injecting fat tissue alone.

A hydrogel composition disclosed herein may show improved volume retention after injection or implantation into a soft tissue. In an embodiment, a hydrogel composition disclosed herein shows improved volume retention after injection or implantation into a soft tissue as compared to a hydrogel composition that is substantially identical except that the hyaluronic acid component and the silk fibroin component are not crosslinked. In some embodiments, a hydrogel composition disclosed herein shows improved volume retention after injection or implantation into a soft tissue by at least about 5% at least about 10%, at least about 15%, at least about 20%, at least about 25%, at least about 30%, at least about 35%, at least about 40%, at least about 45%, or at least about 50% as compared to a hydrogel composition that is substantially identical except that the hyaluronic acid component and the silk fibroin component are not crosslinked. In some embodiments, a hydrogel composition disclosed herein shows improved volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein shows improved volume retention after injection or implantation into a soft tissue as compared to a hydrogel composition that is substantially identical except that the silk fibroin component is absent. In some embodiments, a hydrogel composition disclosed herein shows improved volume retention after injection or implantation into a soft tissue by at least about 5% at least about 10%, at least about 15%, at least about 20%, at least about 25%, at least about 30%, at least about 35%, at least about 40%, at least about 45%, or at least about 50% as compared to a hydrogel composition that is substantially identical except that the silk fibroin component is absent. In some embodiments, a hydrogel composition disclosed herein shows improved volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

A hydrogel composition disclosed herein may show decreased variability in volume retention after injection or implantation into a soft tissue. In an embodiment, a hydrogel composition disclosed herein shows decreased variability in volume retention after injection or implantation into a soft tissue as compared to a hydrogel composition that is substantially identical except that the hyaluronic acid component and the silk fibroin component are not crosslinked. In some embodiments, a hydrogel composition disclosed herein shows decreased variability in volume retention after injection or implantation into a soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the silk fibroin component are not crosslinked. In some embodiments, a hydrogel composition disclosed herein shows decreased variability in volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein shows decreased variability in volume retention after injection or implantation into a soft tissue as compared to a hydrogel composition that is substantially identical except that the silk fibroin component is absent. In some embodiments, a hydrogel composition disclosed herein shows decreased variability in volume retention after injection or implantation into a soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the silk fibroin component is absent. In some embodiments, a hydrogel composition disclosed herein shows decreased variability in volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

Once injected or implanted into a soft tissue, a hydrogel composition disclosed herein may reduce inflammation of the soft tissue. In an embodiment, a hydrogel composition disclosed herein reduces inflammation of the soft tissue as compared to a hydrogel composition that is substantially identical except that the hyaluronic acid component and the silk fibroin component are not crosslinked. In some embodiments, a hydrogel composition disclosed herein reduces inflammation of the soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the hyaluronic acid component and the silk fibroin component are not crosslinked. In some embodiments, a hydrogel composition disclosed herein reduces inflammation of the soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein reduces inflammation of the soft tissue as compared to a hydrogel composition that is substantially identical except that the silk fibroin component is absent. In some embodiments, a hydrogel composition disclosed herein reduces inflammation of the soft tissue by at least about 5% at least about 10%, at least about 15%, at least about 20%, at least 25%, at least about 30%, at least about 35%, at least about 40%, at least about 45%, or at least about 50% as compared to a hydrogel composition that is substantially identical except that the silk fibroin component is absent. In some embodiments, a hydrogel composition disclosed herein reduces inflammation of the soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

A hydrogel or a hydrogel composition may have improved physical properties that may help to encourage cell survival or proliferation. In some embodiments, a hydrogel or a hydrogel composition may allow diffusion of adipose tissue-specific growth factors or pro-angiogenic growth factors to a greater extent than a hydrogel composition comprising hyaluronic acid at a concentration of about 24 mg/mL or about 16 mg/mL and water.

A hydrogel composition disclosed herein may show improved diffusion of adipose tissue-specific growth factors or pro-angiogenic growth factors. In an embodiment, a hydrogel composition disclosed herein shows diffusion of adipose tissue-specific growth factors or pro-angiogenic growth factors to a greater extent as compared to a hydrogel composition that is substantially identical except that the hyaluronic acid component and the silk fibroin component are not crosslinked. In some embodiments, a hydrogel composition disclosed herein shows improved diffusion of adipose tissue-specific growth factors or pro-angiogenic growth factors by at least about 25% at least about 50%, at least about 75%, at least about 100%, at least 125%, at least about 150%, at least about 175%, at least about 200%, at least about 225%, or at least about 250% as compared to a hydrogel composition that is substantially identical except that the hyaluronic acid component and the silk fibroin component are not crosslinked. In some embodiments, a hydrogel composition disclosed herein shows improved diffusion of adipose tissue-specific growth factors or pro-angiogenic growth factors by about 25% to about 100%, about 25% to about 150%, about 25% to about 250%, about 50% to about 100%, about 50% to about 150%, or about 50% to about 250% as compared to a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not crosslinked comprises hyaluronic acid at a concentration of about 16 mg/mL or about 24 mg/mL and water.

In another embodiment, a hydrogel composition disclosed herein shows diffusion of adipose tissue-specific growth factors or pro-angiogenic growth factors to a greater extent as compared to a hydrogel composition that is substantially identical except that the silk fibroin component is absent. In some embodiments, a hydrogel composition disclosed herein shows improved diffusion of adipose tissue-specific growth factors or pro-angiogenic growth factors by at least about 25% at least about 50%, at least about 75%, at least about 100%, at least about 125%, at least about 150%, at least about 175%, at least about 200%, at least about 225%, or at least about 250% as compared to a hydrogel composition that is substantially identical except that the silk fibroin component is absent. In some embodiments, a hydrogel composition disclosed herein shows improved diffusion of adipose tissue-specific growth factors or pro-angiogenic growth factors by about 25% to about 100%, about 25% to about 150%, about 25% to about 250%, about 50% to about 100%, about 50% to about 150%, or about 50% to about 250% as compared to a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

A hydrogel or a hydrogel composition may be used to prepare a space in human or animal tissue. This may be done by injecting a hydrogel or a hydrogel composition into the tissue. After being injected, a hydrogel or a hydrogel composition may degrade over time, such as over a period of about 1 week to about 3 months or about 2 weeks to about 6 weeks, to thereby create the space in the tissue. This may create a fertile nutrient bed through stimulated angiogenesis, cellular ingrowth, secretion of tropic factors, as well as creating space. An anesthetic may also be injected into the tissue, such as before injection of a hydrogel or hydrogel composition, or as part of a hydrogel composition. This may help reduce the pain of injection and allow the procedure to be done as an outpatient procedure.

Once a hydrogel has degraded sufficiently to create a desired space, a human or animal fat composition may be injected into the space in the tissue. A fertile nutrient bed created as described above may help to improve overall fat graft retention as compared to injecting fat without preparing a space as described above.

Some embodiments include a packaged product comprising a device for facilitating introduction, for example, a syringe loaded with a hydrogel and a needle. A syringe may be fitted with a needle of any size that is appropriate for injecting the hydrogel into the soft tissue of interest, such as a needle with about a #25, about a #30, or a larger gauge.

A filler comprising a hydrogel may be suitable for injection if it can be injected into the soft tissue of interest without unreasonable difficulty, and includes fillers that can be dispensed from syringes having gauge as low as about #30 or about #25 under normal manual pressure with a smooth extrusion plateau.

Injection of a hydrogel may provide a soft tissue augmentation that mimics the natural components of the skin. A hydrogel may be injected intradermally or subcutaneously to augment soft tissue and to repair or correct congenital anomalies, acquired defects, or cosmetic defects. Examples of such conditions include congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupis erythematosis), keratotic lesions, enopthalmos in the unucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

A hydrogel may comprise water and a crosslinked macromolecular matrix. Typically, a crosslinked molecular matrix may comprise a hyaluronic acid component and a silk fibroin component, wherein the hyaluronic acid component is crosslinked to the silk fibroin component by a crosslinking component. A crosslinking component may comprise a plurality of crosslink units, wherein at least a portion of the crosslink units comprise an ester bond or an amide bond.

A hydrogel or a hydrogel composition may be at least about 70%, about 93%, or about 96% water by weight, and may approach 100% water by weight. A crosslinked macromolecular matrix may be about 0.01% to about 30%, about 0.1% to about 7%, or about 0.2% to about 4% of the weight of a hydrogel or a hydrogel composition. A hyaluronic acid component may be about 0.005% to about 20%, about 0.1% to about 5% or about 0.2% to about 2.5% of the total weight of a hydrogel or a hydrogel composition. A silk fibroin component may be about 0.01% to about 10%, about 0.03% to about 2%, or about 0.05% to about 1.2% of the total weight of a hydrogel or a hydrogel composition.

A crosslinked macromolecular matrix for a hydrogel may be synthesized by coupling a hyaluronic acid with a silk fibroin using a coupling agent, such as a carbodiimide. In these hydrogels, hyaluronic acid may serve as a biocompatible water-binding component, providing bulk and isovolumetric degradation. Additionally, silk fibroin may impart cell adhesion and signaling domains to promote cell attachment, migration, and other cell functions such as extra-cellular matrix deposition. The biopolymers form homogeneous hydrogels with tunable composition, swelling, and mechanical properties. Compositions can be made to be injectable for minimally invasive implantation through syringe and needle.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid herein may include its fully protonated, or nonionic form as depicted below, as well as any anionic forms and salts of hyaluronic acid, such as sodium salts, potassium salts, lithium salts, magnesium salts, calcium salts, etc.

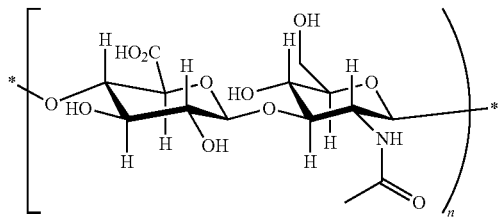

Hyaluronic Acid

Under certain conditions, a hyaluronic acid and a silk fibroin may be combined in an aqueous liquid in which both components are soluble. A hyaluronic acid and a silk fibroin may then be crosslinked while both are dissolved in an aqueous solution to form a hydrogel. Reaction conditions such as the concentration of hyaluronic acid, the concentration of silk fibroin, the pH of the solution, and salt concentration may be adjusted to help to prevent polyionic complex formation between anionic hyaluronic acid and cationic silk fibroin. They may also help to prevent silk fibroin microfibril formation, which results in precipitation from solution and may prevent crosslinking.

Some embodiments include a method of crosslinking hyaluronic acid and silk fibroin. This method generally comprises a dissolution step, which results in an aqueous pre-reaction solution. In a dissolution step, hyaluronic acid and silk fibroin are dissolved in an aqueous solution that has a low pH and/or a salt to form an aqueous pre-reaction solution.

A hyaluronic acid-silk fibroin crosslinking method further comprises an activation step. In an activation step, an aqueous pre-reaction solution is modified by at least adding a water soluble coupling agent and/or by increasing the pH of the solution. If needed, a salt may also be added to keep the hyaluronic acid and silk fibroin in solution at the higher pH. Thus, a crosslinking reaction mixture comprises hyaluronic acid and silk fibroin dissolved or dispersed in an aqueous medium, a water soluble coupling agent, and a salt, and has a higher pH than the aqueous pre-reaction solution from which it was derived. The crosslinking reaction mixture is allowed to react to thereby crosslink the hyaluronic acid and the collagen.

In some embodiments, the pH of the aqueous pre-reaction solution may be increased and a substantial amount of fiber formation may be allowed to occur in the solution before adding the water soluble coupling agent. In some embodiments, the water soluble coupling agent may be added to the aqueous pre-reaction solution before substantially any fiber formation occurs.

A crosslinking reaction mixture can react to form a crosslinked macromolecular matrix. Since reaction occurs in an aqueous solution, a crosslinked macromolecular matrix may be dispersed in an aqueous liquid in hydrogel form as it is formed by a crosslinking reaction. A crosslinked macromolecular matrix may be kept in hydrogel form because, in many instances, a crosslinked macromolecular matrix may be used in hydrogel form.

In some embodiments, an aqueous pre-reaction solution or a crosslinking reaction mixture may further comprise about 10% to about 90% of an organic solvent in which hyaluronic acid has poor solubility, such as ethanol, methanol, isopropanol, or the like.

After a crosslinking reaction has occurred, the crosslinked macromolecular matrix may be particulated or homogenized through a mesh. This may help to form an injectable slurry or hydrogel. A mesh used for particulating a crosslinked macromolecular matrix may have any suitable pore size depending upon the size of particles desired. In some embodiments, the mesh may have a pore size of about 10 microns to about 100 microns, about 50 microns to about 70 microns, or about 60 microns.

A hydrogel comprising a crosslinked molecular matrix may be treated by dialysis for sterilization or other purposes. Dialysis may be carried out by placing a semipermeable membrane between the hydrogel and another liquid so as to allow the hydrogel and the liquid to exchange molecules or salts that can pass through the membrane.

A dialysis membrane may have a molecular weight cutoff that may vary. For example, the cutoff may be about 5,000 daltons to about 100,000 daltons, about 10,000 daltons to about 30,000 daltons, or about 20,000 daltons.

The dialysis may be carried out against a buffer solution, meaning that the liquid on the other side of the membrane from the hydrogel may be a buffer solution. In some embodiments, the buffer solution may be a sterile phosphate buffer solution that may comprise phosphate buffer, potassium chloride, and/or sodium chloride. A sterile phosphate buffer solution may be substantially isosmotic with respect to human physiological fluid. Thus, when dialysis is complete, the liquid component of a hydrogel may be substantially isosmotic with respect to human physiological fluid.

In some embodiments, a crosslinked macromolecular complex may further comprise an aqueous liquid. For example, the crosslinked macromolecular complex may absorb the aqueous liquid so that a hydrogel is formed. An aqueous liquid may comprise water with a salt dissolved in it, such as a phosphate buffer, sodium chloride, potassium chloride, etc. In some embodiments, an aqueous liquid may comprise water, sodium chloride at a concentration of about 100 mM to about 200 mM, potassium chloride at a concentration of about 2 mM to about 3 mM, and phosphate buffer at a concentration of about 5 mM to about 15 mM, wherein the pH of the liquid is about 7 to about 8.

In some embodiments, an anesthetic may be included in any composition comprising a crosslinked macromlecular complex in an amount effective to mitigate pain experienced upon injection of the composition. Examples of an anesthetic may include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. In some embodiments, the at least one anesthetic agent is lidocaine, such as in the form of lidocaine HCl. The concentration of lidocaine may vary. For example, some compositions may have about 0.1% to about 5%, about 0.2% to about 1.0%, or about 0.3% lidocaine by weight (w/w %) of the composition. The concentration of lidocaine in the compositions described herein can be therapeutically effective meaning the concentration may be adequate to provide a therapeutic benefit without inflicting harm to the patient.

A hydrogel may be used in a soft tissue aesthetic product. An aesthetic product includes any product that improves any aesthetic property of any part of an animal or human being. A soft tissue aesthetic product may comprise: an aesthetic device having a form suitable for injecting or implanting into human tissue; and a label comprising instructions to inject or implant the aesthetic component into human tissue; wherein the aesthetic device comprises a crosslinked macromolecular matrix described herein. Some products may comprise the crosslinked macromolecular matrix in hydrogel form.

Some embodiments include a method of improving an aesthetic quality of an anatomic feature of a human being. Improving an aesthetic quality of an anatomic feature of a human being includes improving any kind of aesthetic quality including appearance, tactile sensation, etc., and improving any anatomical feature, including those of the face, limbs, breasts, buttocks, hands, etc. Such a method may comprise injecting or implanting an aesthetic device into a tissue of the human being to thereby improve the aesthetic quality of the anatomic feature; wherein the aesthetic device comprises a crosslinked macromolecular matrix composition described herein. In some embodiments, the crosslinked macromolecular matrix used in the product may be in hydrogel form.

In some embodiments, a hydrogel of a crosslinked macromolecular complex may have a storage modulus of about 1 Pa to about 10,000 Pa, about 50 Pa to 10,000 Pa, about 50 Pa to about 6000 Pa, about 80 Pa to about 2000 Pa, about 500 Pa to about 1000 Pa, about 500 Pa to about 4000 Pa, about 500 Pa to about 5000 Pa, about 556 Pa, about 560 Pa, about 850 Pa, about 852 Pa, about 1000 Pa, or any value in a range bounded by, or between, any of these values.

In some embodiments, a hydrogel of a crosslinked macromolecular complex may have a loss modulus of about 1 Pa to about 500 Pa, about 10 Pa to 200 Pa, about 100 Pa to about 200 Pa, about 20 Pa, about 131 Pa, about 152 Pa, or any value in a range bounded by, or between, any of these values.

In some embodiments, a hydrogel of a crosslinked macromolecular complex may have an average extrusion force of about 10 N to about 50 N, about 20 N to 30 N, or about 25 N, when the hydrogel is forced through a 30 G needle syringe by moving the plunger of a 1 mL syringe containing the hydrogel at a rate of 100 mm/min for about 11 mm, and measuring the average force from about 4 mm to about 10 mm.

A crosslinked macromolecular matrix may have tunable swelling properties based on reaction conditions and hydrogel dilution. In some embodiments, a crosslinked macromolecular matrix may have a swelling ratio of about 20 to about 200. A swelling ratio is the ratio of the weight of the crosslinked macromolecular matrix after synthesis to the weight of the crosslinked macromolecular matrix without any water. The crosslinked macromolecular matrix may have a swelling power of about 1 to about 7. The swelling power is the ratio of the weight of the crosslinked macromolecular matrix when it is saturated with water to the weight of the crosslinked macromolecular matrix after synthesis.

In a crosslinking reaction, the molecular weight of a hyaluronic acid may vary. In some embodiments, a hyaluronic acid may have a molecular weight of about 200,000 daltons to about 10,000,000 daltons, about 500,000 daltons to about 10,000,000 daltons, about 1,000,000 daltons to about 5,000,000 daltons, or about 1,000,000 daltons to about 3,000,000 daltons. When the crosslinking reaction occurs, the resulting crosslinked macromolecular product may have a hyaluronic acid component derived from the hyaluronic acid in the crosslinking reaction. Thus, the ranges recited above may also apply to the molecular weight of a hyaluronic acid component, e.g., about 200,000 daltons to about 10,000,000 daltons, about 500,000 daltons to about 10,000,000 daltons, about 1,000,000 daltons to about 5,000, 000 daltons, or about 1,000,000 daltons to about 3,000,000 daltons. The term "molecular weight" is applied in this situation to a portion of the matrix even though the hyaluronic acid component may not actually be a separate molecule due to the crosslinking. In some embodiments, a higher molecular weight hyaluronic acid may result in a crosslinked molecular matrix that may have a higher bulk modulus and/or less swelling The concentration of hyaluronic acid in an aqueous pre-reaction solution or a crosslinking reaction mixture may vary. In some embodiments, hyaluronic acid is present at about 3 mg/mL to about 100 mg/mL, about 6 mg/mL to about 24 mg/mL, about 1 mg/mL to about 30 mg/mL, about 6 mg/mL, about 9 mg/L, about 12 mg/mL, about 15 mg/L, about 16 mg/mL, about 18 mg/L, about 21 mg/L, or about 24 mg/mL. In some embodiments, higher hyaluronic acid concentration may lead to higher stiffness and/or more swelling in the crosslinked macromolecular matrix.

Silk fibroin concentration in an aqueous pre-reaction solution or a crosslinking reaction mixture may vary. In some embodiments, silk fibroin may be present at a concentration of about 1 mg/mL to about 40 mg/mL, about 1 mg/mL to about 15 mg/mL, about 3 mg/mL to about 12 mg/mL, about 1.7 mg/mL, about 3 mg/mL, about 6 mg/mL, about 8 mg/mL, or about 12 mg/mL.

In some embodiments, the weight ratio of hyaluronic acid to silk fibroin in a aqueous pre-reaction solution or a aqueous pre-reaction solution or a crosslinking reaction mixture (e.g., [wt hyaluronic acid]/[wt collagen]) may be about 0.5 to about 10, about 1 to about 7, about 0.5 to about 3, about 1 to about 3, about 1 to about 2, about 1, about 2, about 3, about 3.5, about 4, about 5, 5.33, about 6, about 7, or any weight ratio in a range bounded by, and/or between, any of these values. When the crosslinking reaction occurs, the resulting crosslinked macromolecular product may have a silk fibroin component derived from the silk fibroin in the crosslinking reaction. Thus, the resulting crosslinked macromolecular matrix may have a weight ratio of hyaluronic acid component to silk fibroin component that corresponds to the weight ratio in the crosslinking reaction, e.g., about 0.5 to about 10, about 1 to about 7, about 0.5 to about 3, about 1 to about 3, about 1 to about 2, about 1, about 2, about 3, about 3.5, about 4, about 5, 5.33, about 6, about 7, or any weight ratio in a range bounded by, and/or between, any of these values. A higher weight ratio of hyaluronic acid to silk fibroin may result in a crosslinked macromolecular matrix with increased swelling, decreased stiffness, and/or decreased cell adhesion.

Certain advantageous compositions of some embodiments include compositions having a hyaluronic acid to silk fibroin weight ratio in the range of about 25:1 to about 1:1. For example, the ratio can be about 20:1, about 19:2, about 18:3, about 17:4, 3:3, about 12:6, about 16:8, about 12:12, about 12:24, about 12:3, about 16:3, or about 20:3 (mg/ml).

In some embodiments, the weight ratio of hyaluronic acid to silk fibroin in a aqueous pre-reaction solution or a aqueous pre-reaction solution or a crosslinking reaction mixture may be about 17 mg/mL of hyaluronic acid to about 4 mg/mL silk fibroin, about 20 mg/mL of hyaluronic acid to about 1 mg/mL silk fibroin, or about 18 mg/mL of hyaluronic acid to about 3 mg/mL silk fibroin.

An increase in the amount of both hyaluronic acid and silk fibroin may result in a crosslinked macromolecular matrix with increased stiffness.

A crosslinking reaction mixture may inlcude non-coordinating buffers. Any non-coordinating buffer may be used that is capable of buffering the mixture and does not form coordinating complexes with coupling agents or metal atoms. Examples of suitable non-coordinating buffers may include, but are not limited to, 2-(N-morpholino)ethanesulfonic acid (MES), 3-(N-morpholino)propanesulfonic acid (MOPS), 4-(2-hydroxyethyl)-1-piperazinyl)ethanesulfonic acid (HEPES), 3-[4-(2-hydroxyethyl)-1-piperazinyl]propanesulfonic acid (HEPPS), N-cyclohexyl-2-aminoethanesulfonic acid (CHES), N-cyclohexyl-3-aminopropanesulfonic acid (CAPS), etc.

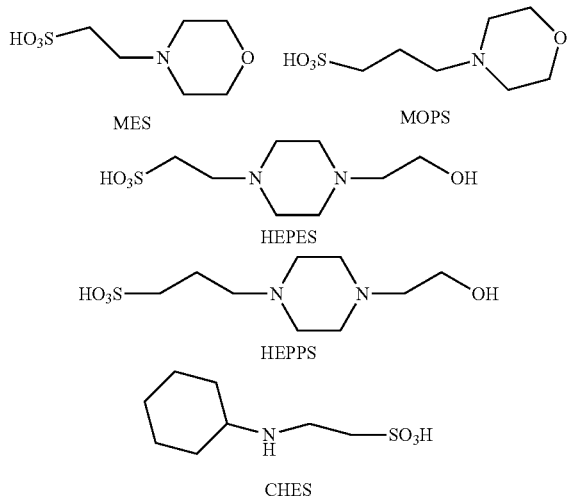

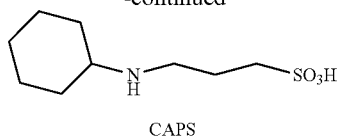

CAPS

The concentration of a non-coordinating buffer may vary. For example, some aqueous pre-reaction solutions or crosslinking reaction mixtures may have a buffer concentration in a range of about 10 mM to about 1 M, about 10 mM to about 500 mM, about 20 mM to about 100 mM, or about 25 mM to about 250 mM. Some aqueous pre-reaction solutions or crosslinking reaction mixtures comprise MES at a concentration of about 20 mM to about 200 mM, about 20 mM to about 100 mM, about 100 mM, or about 180 mM.

Non-buffering salts may also be included in an aqueous pre-reaction solution or a crosslinking reaction mixture as an alternative to, or in addition, to buffering salts. Some examples may include sodium chloride, potassium chloride, lithium chloride, potassium bromide, sodium bromide, lithium bromide, and the like. The concentration of a non-buffering salt may vary. For example, some mixtures may have a non-buffering salt concentration in a range of about 10 mM to about 1 mM, about 30 mM to about 500 mM, or about 50 mM to about 300 mM. In some embodiments, sodium chloride may be present at a concentration in a range of about 0.5% w/v to about 2% about 0.9% w/v, about 1.6% w/v, about 20 mM to about 1 mM, about 40 mM to about 500 mM, about 50 to 300 mM, about 80 mM to about 330 mM, about 150 mM, or about 270 mM.

The pH of an aqueous pre-reaction solution may be lower than the pH of a crosslinking reaction mixture. If the salt content of the aqueous pre-reaction solution is low, the pH may be lower to enhance solubility of the hyaluronic acid and the silk fibroin. If the salt content is higher, the pH may be higher in the aqueous pre-reaction solution. In some embodiments, the pH of the aqueous pre-reaction mixture is about 1 to about 8, about 3 to about 8, about 4 to about 6, about 4.7 to about 7.4, or about 5.4. For low salt concentrations, the pH may be about 1 to about 4 or about 1 to about 3. In some embodiments, a pH of around 5.4 may result in a crosslinked macromolecular matrix having higher stiffness and/or lower swelling.

Any water-soluble coupling agent may be used that can crosslink hyaluronic acid to silk fibroin. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl)carbodiimide (EDC), etc. Carbodiimide coupling agents may facilitate ester or amide bond formation without becoming part of the linkage. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM.

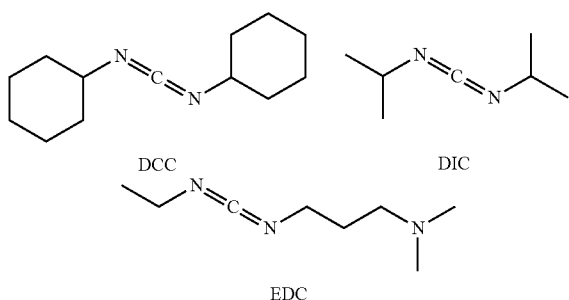

DCC  DIC  EDC

An activating agent may be used to increase the rate of the crosslinking reaction and the number of crosslink units in the final product. In some embodiments, an activating agent may be a triazole such as hydroxybenzotriazole (HOBT) or 1-hydroxy-7-azabenzotriazole (HOAT); a fluorinated phenol such as pentafluorophenol; a succinimide such as N-hydroxysuccinimide (NHS) or N-hydroxysulfosuccinimide (sulfoNHS), and the like.

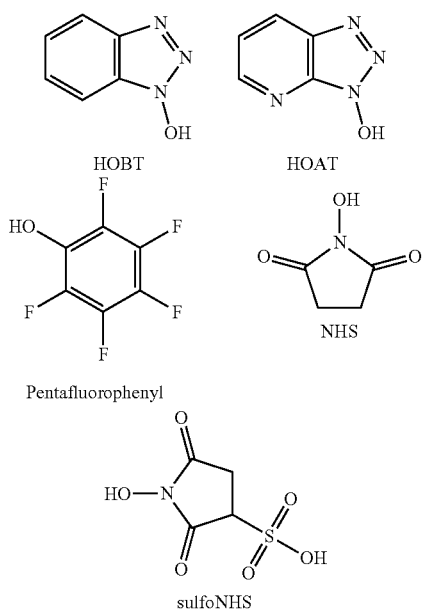

HOBT  HOAT

Pentafluorophenyl  NHS sulfoNHS

The concentration of an activating agent may vary. In some embodiments, the activating agent may have a concentration of about 2 mM to about 200 mM, about 2 mM to about 50 mM, about 20 mM to about 100 mM, or about 50 mM. In some embodiments, the activating agent may be NHS or sulfoNHS is at a concentration of about 2 mM to about 50 mM. In some embodiments, the activating agent may be N-hydroxysulfosuccinimide, sodium salt, at a concentration of about 20 mM to about 100 mM, or about 50 Mm.

Crosslinking HA via EDC chemistry involves the use of small multi amine cross linkers, which form amide bonds with the carboxylic functional groups of HA chains. In ideal condition, EDC activates the carboxylic acid groups of HA, and the activated carboxylic acid groups then react with the amines. Crosslinking is usually done at pH between 4-7 and temperatures between 20 and 37° C., conditions at which degradation of HA is minimal. Linear diamine cross linkers like hexamethylene diamine (HMDA), lysine, lysine methyl ester or lysine ethyl ester, have been used to crosslink HA for various applications. Protein additives with high lysine content such as Collagen can also be used. Crosslinking HA via EDC chemistry without the use of a multiamine cross linker results in the formation of ester bonds between carboxylic acid groups and the hydroxyl groups of HA. Ester bonds are very labile, and are easily hydrolyzed at high temperatures. HA hydrogels made by ester cross linking are generally not robust and cannot be sterilized with moist steam.

The present disclosure includes a composition comprising a gel phase including a hydrogel comprising a silk fibroin covalently attached to an HA ("the composition").

The silk fibroin used for preparing the composition is an intermediate in the silk hydrogel production process and a direct precursor to the hydrogel material. The depolymerized silk fibroin can be made from raw cocoons, previously degummed silk or any other partially cleaned silk. This may also include material commonly termed as "waste" from the reeling process, i.e., short fragments of raw or degummed silk, the sole precaution being that the silk must be substantially cleaned of sericin prior to making fibroin solution and inducing gel formation. A particular source of raw silk is from common domesticated silkworm *B. mori*, though several other sources of silk may be appropriate. This includes other strains of Bombycidae including *Antheraea pernyi*, *Antheraea yamamai*, *Antheraea mylitta*, *Antheraea assama*, and *Philosamia cynthia ricini*, as well as silk producing members of the families Saturnidae, Thaumetopoeidae, and silk-producing members of the order Araneae. The material may also be obtained from other spider, caterpillar, or recombinant sources.

A hydrogel disclosed herein provides for a depolymerized silk fibroin and/or silk fibroin that are substantially free of sericin. Methods for performing sericin extraction have been described in pending U.S. patent application Ser. No. 10/008,924, U.S. Publication No. 2003/0100108, Matrix for the production of tissue engineered ligaments, tendons and other tissue. That application refers to cleaned fibroin fibers spun into yarns, used to create a porous, elastic matrix suitable as a substrate for applications requiring very high tensile strength, such as bioengineered ligaments and tendons.

Extractants such as urea solution, hot water, enzyme solutions including papain among others, which are known in the art to remove sericin from fibroin would also be acceptable for generation of the silk. Mechanical methods may also be used for the removal of sericin from silk fibroin. This includes but is not limited to ultrasound, abrasive scrubbing and fluid flow. The rinse post-extraction is conducted preferably with vigorous agitation to remove substantially any ionic contaminants, soluble, and in soluble debris present on the silk as monitored through microscopy and solution electrochemical measurements. A criterion is that the extractant predictably and repeatably remove the sericin coat of the source silk without significantly compromising the molecular structure of the fibroin. For example, an extraction may be evaluated for sericin removal via mass loss, amino acid content analysis, and scanning electron microscopy. Fibroin degradation may in turn be monitored by FTIR analysis, standard protein gel electrophoresis and scanning electron microscopy.

In certain cases, the silk utilized for making the composition has been substantially depleted of its native sericin content (i.e., ≤4% (w/w) residual sericin in the final extracted silk). Alternatively, higher concentrations of residual sericin may be left on the silk following extraction or the extraction step may be omitted. In preferred some embodiments, the sericin-depleted silk fibroin has, e.g., about 0% to about 4% (w/w) residual sericin. In the most preferred some embodiments, the sericin-depleted silk fibroin has, e.g., about 1% to 3% (w/w) residual sericin.

In certain cases, the silk utilized for generation of a silk hydrogel is entirely free of its native sericin content. As used herein, the term "entirely free (i.e., "consisting of" terminology) means that within the detection range of the instrument or process being used, the substance cannot be detected or its presence cannot be confirmed.

The water soluble or dissolved silk can be prepared by a 4 hour digestion at 60° C. of pure silk fibroin at a concentration of 200 g/L in a 9.3 M aqueous solution of lithium bromide to a silk concentration of 20% (w/v). This process may be conducted by other means provided that they deliver a similar degree of dissociation to that provided by a 4 hour digestion at 60° C. of pure silk fibroin at a concentration of 200 g/L in a 9.3 M aqueous solution of lithium bromide. The primary goal of this is to create uniformly and repeatably dissociated silk fibroin molecules to ensure similar fibroin solution properties and, subsequently, device properties. Less substantially dissociated silk solution may have altered gelation kinetics resulting in differing final gel properties. The degree of dissociation may be indicated by Fourier-transform Infrared Spectroscopy (FTIR) or x-ray diffraction (XRD) and other modalities that quantitatively and qualitatively measure protein structure. Additionally, one may confirm that heavy and light chain domains of the silk fibroin dimer have remained intact following silk processing and dissolution. This may be achieved by methods such as standard protein sodium-dodecyl-sulfate polyacrylamide gel electrophoresis (SDS-PAGE), which assess molecular weight of the independent silk fibroin domains.

System parameters which may be modified in the initial dissolution of silk include but are not limited to solvent type, silk concentration, temperature, pressure, and addition of mechanical disruptive forces. Solvent types other than aqueous lithium bromide may include but are not limited to aqueous solutions, alcohol solutions, 1,1,1,3,3,3-hexafluoro-2-propanol, and hexafluoroacetone, 1-butyl-3-methylimidazolium. These solvents may be further enhanced by addition of urea or ionic species including lithium bromide, calcium chloride, lithium thiocyanate, zinc chloride, magnesium salts, sodium thiocyanate, and other lithium and calcium halides would be useful for such an application. These solvents may also be modified through adjustment of pH either by addition of acidic of basic compounds.

Cross-linking can also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and Immuno Technology Catalogue and Handbook, Pierce Chemical Co. (1989), each of which is incorporated herein by reference. Such conjugation, including cross-linking, should be performed so as not to substantially affect the desired function of the peptide oligomer or entity conjugated thereto, including therapeutic agents, and moieties capable of binding substances of interest.

It will be apparent to one skilled in the art that alternative linkers can be used to link peptides, for example the use of chemical protein crosslinkers. For example homobifunctional crosslinker such as disuccinimidyl-suberimidate-dihydrochloride; dimethyl-adipimidate-dihydrochloride; 1,5,-2,4dinitrobenezene or heterobifunctional crosslinkers such as N-hydroxysuccinimidyl 2,3-dibromopropionate; 1ethyl-3-[3-dimethylaminopropyl]carbodiimide hydrochloride; and succinimidyl4-[n-maleimidomethyl]-cyclohexane-1-carboxylate.

A composition disclosed herein is typically biodegradable, bioerodible, and/or bioresorbable. In an embodiment, a silk fibroin cross linked to a hyaluronic acid hydrogel disclosed herein has a protein structure that makes the hydrogel resist biodegradation, bioerosion, and/or bioresorption. In some embodiments, a hydrogel is resistant to biodegradation, bioerosion, and/or bioresorption for, e.g., between about 10 days to about 180 days. In some embodiments, a hydrogel is resistant to biodegradation, bioerosion, and/or bioresorption for, e.g., about 30 day to about 90 days. In some embodiments, a hydrogel is resistant to biodegradation, bioerosion, and/or bioresorption for, e.g., about 20 days to 90 days.

In yet another embodiment, a silk fibroin hydrogel disclosed herein has a protein structure that substantially includes β-turn and β-strand regions. In some embodiments, a hydrogel has a protein structure including, e.g., between about 10% to about 100% β-turn and β-strand regions. In some embodiments, a hydrogel has a protein structure including, e.g., between about 20% to about 70% β-turn and β-strand regions. In some embodiments, a hydrogel has a protein structure including, e.g., between about 30% to about 50% β-turn and β-strand regions.

In yet another embodiment, a silk fibroin hydrogel disclosed herein has a protein structure that is substantially-free of α-helix and random coil regions. In some embodiments, a hydrogel has a protein structure including, e.g., between about 5% to about 50% α-helix and random coil regions. In some preferred some embodiments, a hydrogel has a protein structure including, e.g., between about 10% to about 40% α-helix and random coil regions. In the most preferred some embodiments, a hydrogel has a protein structure including, e.g., between about 15% to about 35% α-helix and random coil regions.

Aspects of the present specification provide, in part, a silk fibroin hydrogel having hardness. Hardness refers to various properties of an object in the solid phase that gives it high resistance to various kinds of shape change when force is applied. Hardness is measured using a durometer and is a unitless value that ranges from zero to 100. The ability or inability of a hydrogel to be easily compressed will affect its suitability for application in different tissue replacement roles, i.e., mechanical compliance as bone, fat, connective tissue. Hardness will also affect the ability of a hydrogel to be effectively comminuted, the reason being that a hard material may be more easily and consistently comminuted. Hardness will also affect extrudability, as a soft material may be more readily able to be slightly compressed during injection to pack with other particles or change shape to pass through a syringe barrel or needle.

In an embodiment, a silk fibroin hydrogel exhibits low hardness. In some embodiments, a silk fibroin hydrogel exhibits a hardness of, e.g., between about 5 to about 40. In some preferred some embodiments, a silk fibroin hydrogel exhibits a hardness of, e.g., between about 10 to about 30. In the most preferred some embodiments, a silk fibroin hydrogel exhibits a hardness of, e.g., between about 15 to about 35.

In an embodiment, a silk fibroin hydrogel exhibits medium hardness. In some embodiments, a silk fibroin hydrogel exhibits a hardness of, e.g., about 40 to about 65. In some preferred some embodiments, a silk fibroin hydrogel exhibits a hardness of, e.g., about 30 to about 55. In the most preferred some embodiments, a silk fibroin hydrogel exhibits a hardness of, e.g., about 45 to about 60.

In another embodiment, a silk fibroin hydrogel exhibits high hardness. In some embodiments, a silk hydrogel exhibits a hardness of, e.g., between about 65 to about 95. In some preferred some embodiments, a silk hydrogel exhibits a hardness of, e.g., between about 70 to about 90. In the most preferred some embodiments, a silk hydrogel exhibits a hardness of, e.g., between about 75 to about 85.

In an embodiment, a silk fibroin hydrogel exhibits high resistance to deformation. In some embodiments, a silk fibroin hydrogel exhibits resistant to deformation of, e.g., about 100% to about 85%. In some preferred some embodiments, a silk fibroin hydrogel exhibits resistant to deformation of, e.g., about 95% to about 80%. In the most preferred some embodiments, a silk fibroin hydrogel exhibits resistant to deformation of, e.g., about 93% to about 78%.

A silk fibroin hydrogel exhibits an elastic modulus. Elastic modulus, or modulus of elasticity, refers to the ability of a hydrogel material to resists deformation, or, conversely, an object's tendency to be non-permanently deformed when a force is applied to it. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a silk fibroin hydrogel exhibits a tensile and/or shear modulus. In some embodiments, a silk fibroin hydrogel exhibits a tensile modulus of, e.g., about 1 MPa to about 30 GPa. In some preferred some embodiments, a silk fibroin hydrogel exhibits a tensile modulus of, e.g., about 5 MPa to about 25 GPa. In some embodiments, a silk fibroin hydrogel exhibits a tensile modulus of about 20 MPa to about 15 GPa.

In another embodiment, a silk fibroin hydrogel exhibits a bulk modulus. In some embodiments, a silk fibroin hydrogel exhibits a bulk modulus of, e.g., about 5 GPa to about 100 GPa. In some preferred some embodiments, a silk fibroin hydrogel exhibits a bulk modulus of, e.g., about 10 GPa to about 90 GPa. In the most preferred some embodiments, a silk fibroin hydrogel exhibits a bulk modulus of, e.g., about 25 GPa to about 85 GPa.

A silk fibroin hydrogel exhibits high tensile strength. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a silk fibroin hydrogel exhibits high yield, high ultimate, and/or high breaking strength relative to other polymer classes. In some embodiments, a silk fibroin hydrogel exhibits a yield strength of, e.g., about 0.1 MPa to about 500 MPa. In some preferred some embodiments, a silk fibroin hydrogel exhibits a yield strength of, e.g., about 5 MPa to about 400 MPa. In the most preferred some embodiments, a silk fibroin hydrogel exhibits a yield strength of e.g., about 20 MPa to about 300 MPa.

Aspects of the present specification provide, in part, a silk fibroin hydrogel having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, silk fibroin concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As a result, an optically transparent material allows much of the light that falls on it to be transmitted, with little light being reflected. Materials which do not allow the transmission of light are called optically opaque or simply opaque.

In an embodiment, a silk fibroin hydrogel is optically transparent. In some embodiments, a silk fibroin hydrogel transmits, e.g., between about 75% to about 100% of the light. In some preferred some embodiments, a silk fibroin hydrogel transmits, e.g., between about 80% to about 90% of the light. In the most preferred some embodiments, a silk fibroin hydrogel transmits, e.g., between about 85% to about 90% of the light.

In another embodiment, a silk fibroin hydrogel is optically opaque. In some embodiments, a silk fibroin hydrogel transmits, e.g., between about 5% to about 75% of the light. In some preferred some embodiments, a silk fibroin hydrogel transmits, e.g., between about 10% to about 70% of the light. In the most preferred some embodiments, a silk fibroin hydrogel transmits, e.g., between about 15% to about 65% of the light.

In an embodiment, a silk fibroin hydrogel is optically translucent. In some embodiments, a silk fibroin hydrogel diffusely transmits, e.g., between about 75% to about 100% of the light. In some preferred some embodiments, a silk fibroin hydrogel diffusely transmits, e.g., between about 80% to about 95% of the light. In some the most preferred some embodiments, a silk fibroin hydrogel diffusely transmits, e.g., between about 85% to about 95% of the light.

After formation of a hydrogel described herein, the hydrogel can further processed. For example, to remove enhancer species and become a more complete, the formed hydrogel may be leeched against a solvent, such as, e.g., water, under ambient temperature and pressure conditions for three days with five changes of water. The hydrogel may be leeched against ultra-pure water of a volume at least 100-times that of the gel. More specifically, for example, the gels may be placed in a bulk of purified water and the rinse changed at hours 12, 24 and 48 with 15 mL gel per 1.5 L water. The number of rinses and volume ratios involved may be altered so long as the resultant hydrogel is substantially free of residual gelation enhancer.

A composition disclosed herein may be formulated using material processing constraints such as silk concentration and saline concentration to tailor material longevity in vivo. In one example, a silk hydrogel might be tailored for a persistence of five weeks to six weeks in vivo by using a 1%-3% (w/v) silk gel with 25%-50% (v/v) saline carrier. In another example, a silk hydrogel might be tailored for a persistence of two months to three months in vivo by using a 3%-5% (w/v) silk gel with 20%-40% (v/v) saline. In another example, a silk hydrogel might be tailored for a persistence of 5-6 months by using 4-6% (w/v) silk gel with 20-40% (v/v) saline. In another example, a silk hydrogel might be tailored for a persistence of 7-10 months by using a 6-8% (w/v) silk gel with 20-30% (v/v) saline. The persistence of these materials might also be increased or decreased by increasing or decreasing particle size respectively.

Gel emulsion saline content and gel silk concentration could be used to modify the mechanical profile of the silk gel materials for particular applications. For example, a gel emulsion of about 1% (w/v) to about 5% (w/v) silk gel concentration with 5%-95% lubricant (e.g., 5%-95% (w/v) saline/PBS) may be useful as a dermal filler, bulking agent, camouflage agent, intramuscular or sub-Q filler, or pharmaceutical delivery vector. A gel emulsion of, for example, about 5% (w/v) to about 8% (w/v) silk gel concentration with 0% to about 30% lubricant fluid may be useful in bone defects or cartilage defects.

Aspects of the present specification provide, in part, a composition comprising a gel phase including a hydrogel comprising a matrix polymer. The compositions disclosed herein can further comprise a hydrogel comprising one or more matrix polymers in addition to hydrogel particles comprising silk fibroin, or a hydrogel comprising one or more matrix polymers and silk fibroin. As used herein, the term "matrix polymer" refers to a polymer that can become part of and/or function as an extracellular matrix polymer and pharmaceutically acceptable salts thereof. Non-limiting examples of a matrix polymer include a glycosaminoglycan like chondroitin sulfate, dermatan sulfate, keratan sulfate, hyaluronan; a lubricin; a polysaccharide, and an elastic protein (like silk protein, resilin, resilin-like polypeptides (RLPs), elastin (including tropoelastin, fibrillin and fibullin), elastin-like polypeptides (ELPs), gluten (including gliadin and glutenin), abductin, byssus, and collagen). Non-limiting examples of a pharmaceutically acceptable salt of a matrix polymer includes sodium salts, potassium salts, magnesium salts, calcium salts, and combinations thereof. Matrix polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

Aspects of the present specification provide, in part, a composition comprising a hyaluronan. As used herein, the term "hyaluronic acid" is synonymous with "HA", "hyaluronic acid", and "hyaluronate" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan can be purified from animal and non-animal sources. Polymers of hyaluronan can range in size from about 5,000 Da to about 20,000,000 Da. Any hyaluronan is useful in the compositions disclosed herein with the proviso that the hyaluronan improves a condition of the skin, such as, e.g., hydration or elasticity. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a composition comprising a crosslinked matrix polymer. As used herein, the term "crosslinked" refers to the intermolecular bonds joining the individual polymer molecules, or monomer chains, into a more stable structure like a gel. As such, a crosslinked matrix polymer has at least one intermolecular bond joining at least one individual polymer molecule to another one. Matrix polymers disclosed herein may be crosslinked using dialdehydes and disufides crosslinking agents including, without limitation, multifunctional PEG-based cross linking agents, divinyl sulfones, diglycidyl ethers, and bis-epoxides. Non-limiting examples of hyaluronan crosslinking agents include divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, or combinations thereof.

Aspects of the present specification provide, in part, a composition comprising a crosslinked matrix polymer having a degree of crosslinking. As used herein, the term "degree of crosslinking" refers to the percentage of matrix polymer monomeric units that are bound to a cross-linking agent, such as, e.g., the disaccharide monomer units of hyaluronan. Thus, a composition that that has a crosslinked matrix polymer with a 4% degree of crosslinking means that on average there are four crosslinking molecules for every 100 monomeric units. Every other parameter being equal, the greater the degree of crosslinking, the harder the gel becomes. Non-limiting examples of a degree of crosslinking include about 1% to about 15%.

In an embodiment, a composition comprises an uncrosslinked hyaluronan where the uncrosslinked hyaluronan comprises a combination of both high molecular weight hyaluronan and low molecular weight hyaluronan in a ratio of about 20:1, about 15:1, about 10:1, about 5:1, about 1:1, about 1:5 about 1:10, about 1:15, or about 1:20.

In another embodiment, a composition comprises an uncrosslinked hyaluronan where the uncrosslinked hyaluronan comprises a combination of both high molecular weight hyaluronan and low molecular weight hyaluronan, in various ratios. As used herein, the term "high molecular weight hyaluronan" refers to a hyaluronan polymer that has a molecular weight of 1,000,000 Da or greater. Non-limiting examples of a high molecular weight hyaluronan include a hyaluronan of about 1,500,000 Da, a hyaluronan of about 2,000,000 Da, a hyaluronan of about 2,500,000 Da, a hyaluronan of about 3,000,000 Da, a hyaluronan of about 3,500,000 Da, a hyaluronan of about 4,000,000 Da, a hyaluronan of about 4,500,000 Da, and a hyaluronan of about 5,000,000 Da. As used herein, the term "low molecular weight hyaluronan" refers to a hyaluronan polymer that has a molecular weight of less than 1,000,000 Da. Non-limiting examples of a low molecular weight hyaluronan include a hyaluronan of about 200,000 Da, a hyaluronan of about 300,000 Da, a hyaluronan of about 400,000 Da, a hyaluronan of about 500,000 Da, a hyaluronan of about 600,000 Da, a hyaluronan of about 700,000 Da, a hyaluronan of about 800,000 Da, and a hyaluronan of about 900,000 Da.

In other some embodiments, a composition comprises a crosslinked hyaluronan where the crosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other some embodiments, a composition comprises a crosslinked hyaluronan where the crosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other some embodiments, a composition comprises a crosslinked hyaluronan where the crosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

In other some embodiments, a composition comprises an uncrosslinked hyaluronan where the uncrosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other some embodiments, a composition comprises an uncrosslinked hyaluronan where the uncrosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other some embodiments, a composition comprises an uncrosslinked hyaluronan where the uncrosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In some embodiments, a composition comprises an uncrosslinked hyaluronan where the uncrosslinked hyaluronan has a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

A composition disclosed herein comprises a gel phase including a silk fibroin hydrogel component or particle and matrix polymer hydrogel component or particle. In some embodiments, the percent amount of silk fibroin hydrogel present in a composition relative to matrix polymer hydrogel is from about 0.1% (v/v) to about 25% (v/v). In some embodiments, the percent amount of matrix polymer hydrogel present in a composition relative to silk fibroin hydrogel is from about 99.9% (v/v) to about 75% (v/v). In some embodiments, the ratio of silk fibroin hydrogel to matrix polymer hydrogel in the gel phase of a composition comprises, e.g., about 0.1% (v/v) silk fibroin hydrogel and about 99.9% (v/v) matrix polymer hydrogel, about 1% (v/v) silk fibroin hydrogel and about 99% (v/v) matrix polymer hydrogel, about 5% (v/v) silk fibroin hydrogel and about 95% (v/v) matrix polymer hydrogel, about 10% (v/v) silk fibroin hydrogel and about 90% (v/v) matrix polymer hydrogel, about 15% (v/v) silk fibroin hydrogel and about 85% (v/v) matrix polymer hydrogel, about 20% (v/v) silk fibroin hydrogel and about 80% (v/v) matrix polymer hydrogel, or about 25% (v/v) silk fibroin hydrogel and about 75% (v/v) matrix polymer hydrogel.

A composition disclosed herein may comprise a gel phase where the silk fibroin hydrogel component and matrix polymer hydrogel component are processed separately. The resulting processed hydrogel materials, e.g., hydrogel particles of both types, are then mixed together, such as, e.g., after a milling step and/or after re-homogenization in a carrier phase, to form the final composition. In addition, a matrix polymer may be initially mixed with depolymerized silk fibroin solution, with subsequent polymerization occurring only after the completion of the mixing step to form an integrated matrix polymer/silk fibroin composite hydrogel. Similarly, the silk fibroin and matrix polymers may be linked together to form a hydrogel composite that is then subsequently processed into the gel phase of the composition. Such linkage can occur by a typical cross linking method or by linking the matrix polymer to the silk fibroin hydrogel via a peptide linker disclosed herein, such as, e.g., a five-amino acid peptide "tail" and synthetic molecule. As disclosed herein, a composition may comprise a gel phase that comprises both separately processed hydrogel components as well as particles of hydrogel composites.

As a non-limiting example, a solution comprising about 1% to about 30% depolymerized silk fibroin may be mixed with about 6 mg/g to about 30 mg/g of hyaluronan having a degree of cross linking of from 0 to about 17% where the percent weight of the silk fibroin component is from about 1% to about 75%. As another non-limiting example, hydrogel particles comprising from about 1% to about 8% silk fibroin are mixed with hydrogel particles comprising about 6 mg/g to about 30 mg/g of hyaluronan having a degree of cross linking of from 0 to about 17% where the percent weight of the silk fibroin component is from about 1% to about 75%. As yet another non-limiting example, a hydrogel composition comprising hydrogel particles comprising from about 1% to about 8% silk fibroin mixed together with a carrier phase (about 20% (v/v) to about 50% (v/v)) is mixed with a hydrogel composition comprising hydrogel particles comprising about 6 mg/g to about 30 mg/g of hyaluronan having a degree of cross linking of from 0 to about 17% where the percent weight of the silk fibroin component is from about 1% to about 75%.

Aspects of the present specification provide, in part, a composition comprising a silk fibroin hydrogel component or particle and matrix polymer hydrogel component or particle having opacity. Opacity is the measure of impenetrability to electromagnetic or other kinds of radiation, especially visible light. An opaque object is neither transparent (allowing all light to pass through) nor translucent (allowing some light to pass through). In certain applications, it would be an advantage to have an opaque composition. For example, in applications where a composition disclosed herein is administered to a superficial region, an opaque composition provides coloration and appearance of the overlying skin.

In an embodiment, a composition comprising a silk fibroin hydrogel and a polymer matrix is optically opaque. In some embodiments, a composition comprising a silk fibroin hydrogel and a polymer matrix transmits, e.g., about 5% of the light to about 70% of the light. In some preferred some embodiments, a composition comprising a silk fibroin hydrogel and a polymer matrix transmits, e.g., about 10% of the light to about 65% of the light. In the most preferred some embodiments, a composition comprising a silk fibroin hydrogel and a polymer matrix transmits, e.g., about 15% of the light to about 60% of the light.

In some embodiments, a composition comprising a silk fibroin hydrogel and a polymer matrix exhibits, e.g., about 5% to about 100% reduction in tyndalling. In some preferred some embodiments, a composition comprising a silk fibroin hydrogel and a polymer matrix exhibits, e.g., about 10% to about 95% reduction in tyndalling. In the most preferred some embodiments, a composition comprising a silk fibroin hydrogel and a polymer matrix exhibits, e.g., about 15% to about 90% reduction in tyndalling.

Aspects of the present specification provide, in part, a composition disclosed herein exhibiting a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity ($\mu$, although $\eta$ is sometimes used) or kinematic viscosity ($v$). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m-2·s. Dynamic viscosity can be expressed as $\tau=\mu\, dvx/dz$, where $\tau$=shearing stress, $\mu$=dynamic viscosity, and $dvx/dz$ is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity ($v$) is the ratio of dynamic viscosity to density, a quantity in which no force is involved and is defined as follows: $v=\mu/\rho$, where $\mu$ is the dynamic viscosity $\rho$ is density with the SI unit of $kg/m^3$. Kinematic viscosity is usually measured by a glass capillary viscometer as has an SI unit of $m^2/s$.

The viscosity of a fluid is highly temperature dependent and for either dynamic or kinematic viscosity to be meaningful, the reference temperature must be quoted. For the viscosity values disclosed herein, a dynamic viscosity is measured at 1 Pa with a cone/plane geometry 2°/40 cm and a temperature of 20° C. Examples of the dynamic viscosity of various fluids at 20° C. is as follows: water is about $1.0\times10^{-3}$ Pa·s, blood is about $3\text{-}4\times10^{-3}$ Pa·s, vegetable oil is about $60\text{-}85\times10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

In some embodiments, a composition disclosed herein exhibits a dynamic viscosity of, e.g., about 10 Pa·s to about 1,200 Pa·s. In some preferred some embodiments, a composition disclosed herein exhibits a dynamic viscosity of, e.g., about 20 Pa·s to about 1,100 Pa·s. In the most preferred some embodiments, a composition disclosed herein exhibits a dynamic viscosity of, e.g., about 30 Pa·s to about 1,000 Pa·s.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In some embodiments, a composition disclosed herein is injectable through a fine needle. In other some embodiments, a composition disclosed herein is injectable through a needle of, e.g., about 27 gauge, about 30 gauge, or about 32 gauge. In yet other some embodiments, a composition disclosed herein is injectable through a needle of, e.g., 27 gauge or smaller, 30 gauge or smaller, or 32 gauge or smaller. In still other some embodiments, a composition disclosed herein is injectable through a needle of, e.g., about 27 gauge to about 32 gauge.

In some embodiments, a composition disclosed herein can be injected with an extrusion force of about 60 N to about 5 N or less. In some preferred some embodiments, a composition disclosed herein can be injected with an extrusion force of about 55 N to about 10 N or less. In the most preferred some embodiments, a composition disclosed herein can be injected with an extrusion force of about 50 N to about 15 N or less.

Aspects of the present specification provide, in part, a composition disclosed herein exhibits cohesiveness. Cohesion or cohesive attraction, cohesive force, or compression force is a physical property of a material, caused by the intermolecular attraction between like-molecules within the material that acts to unite the molecules. A composition should be sufficiently cohesive as to remain localized to a site of administration. Additionally, in certain applications, a sufficient cohesiveness is important for a composition to retain its shape, and thus functionality, in the event of mechanical load cycling. As a result, in one embodiment, a composition exhibits strong cohesive attraction, on par with water. In another embodiment, a composition exhibits low cohesive attraction. In yet another embodiment, a composition exhibits sufficient cohesive attraction to remain localized to a site of administration. In still another embodiment, a composition exhibits sufficient cohesive attraction to retain its shape. In a further embodiment, a composition exhibits sufficient cohesive attraction to retain its shape and functionality.

In some embodiments, a composition disclosed herein has a compression force of about 10 grams-force to about 3000 grams-force. In some preferred some embodiments, a composition disclosed herein has a compression force of about 20 grams-force to about 2000 grams-force. In the most preferred of this embodiment, a composition disclosed herein has a compression force of about 30 grams-force to about 1000 grams-force.

Aspects of the present specification provide, in part, a method of treating a soft tissue condition of an individual by administering a composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a compound disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A composition or compound is administered to an individual. An individual is typically a human being. Typically, any individual who is a candidate for a conventional procedure to treat a soft tissue condition is a candidate for a method disclosed herein. In addition, the presently disclosed compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

The amount of a composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

The amount of a composition used with any of the methods disclosed herein will typically be a therapeutically effective amount. As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As a non-limiting example, an effective amount is an amount sufficient to achieve one or more of the clinical and/or cosmetic measures disclosed herein. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a composition disclosed herein that is administered can be adjusted accordingly.

In some embodiments, the amount of a composition administered is, e.g., 0.01 g, 0.05 g, 0.1 g, 0.5 g, 1 g, 5 g, 10 g, 20 g, 30 g, 40 g, 50 g, 60 g, 70 g, 80 g, 90 g, 100 g, 150 g, or 200 g. In other some embodiments, the amount of a composition administered is, e.g., about 0.01 g to about 0.1 g, about 0.1 g to about 1 g, about 1 g to about 10 g, about 10 g to about 100 g, or about 50 g to about 200 g. In yet other some embodiments, the amount of a composition administered is, e.g., 0.01 mL, 0.05 mL, 0.1 mL, 0.5 mL, 1 mL, 5 mL, 10 mL, 20 mL, 30 mL, 40 mL, 50 mL, 60 mL, 70 g, 80 mL, 90 mL, 100 mL, 150 mL, or 200 mL. In other some embodiments, the amount of a composition administered is, e.g., about 0.01 mL to about 0.1 mL, about 0.1 mL to about 1 mL, about 1 mL to about 10 mL, about 10 mL to about 100 mL, or about 50 mL to about 200 mL.

Aspects of some embodiments provide, in part, administering a composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In some embodiments, a composition disclosed herein is administered to a skin region of an individual by injection.

The route of administration of composition administered to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, catheter, topically, or by direct surgical implantation. The composition disclosed herein can be administered into a skin region such as, e.g., a dermal region or a hypodermal region. In addition, a composition disclosed herein can be administered once, or over a plurality of times. Ultimately, the timing used will follow quality care standards.

For a breast soft tissue replacement procedure, the route of administration may include axillary, periareolar, and/or inframammary routes. Alternatively or in addition, a composition may be delivered through a transaxillary endoscopic subpectoral approach. For a facial soft tissue replacement procedure, the route of administration can be frontal, temporal, zygomatic, periocular, amdibula, perioral or chin routes. In urinary incontinence procedures, the route of administration may include transurethral or periurethral routes. Alternatively or in addition, administration may be delivered via an antegrade route. The routes discussed herein do not exclude the use of multiple routes to achieve the desired clinical effect.

Aspects of some embodiments provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In some embodiments, a composition disclosed herein is administered to a skin region of an individual by injection into a dermal region or a hypodermal region. In some embodiments, a composition disclosed herein is administered to a dermal region of an individual by injection into, e.g., an epidermal-dermal junction region, a papillary region, a reticular region, or any combination thereof.

Aspects of the present specification disclose, in part, a method of treating a soft tissue condition of an individual, the method comprising the steps of administering a composition disclosed herein to a site of the soft tissue condition of the individual, wherein the administration of the composition improves the soft tissue condition, thereby treating the soft tissue condition. In some embodiments, a soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Some embodiments relate at least in part to a method of treating a skin condition comprises the step of administering to an individual suffering from a skin condition a composition disclosed herein, wherein the administration of the composition improves the skin condition, thereby treating the skin condition. In some embodiments, a skin condition is a method of treating skin dehydration comprises the step of administering to an individual suffering from skin dehydration a composition disclosed herein, wherein the administration of the composition rehydrates the skin, thereby treating skin dehydration. In some embodiments, a method of treating a lack of skin elasticity comprises the step of administering to an individual suffering from a lack of skin elasticity a composition disclosed herein, wherein the administration of the composition increases the elasticity of the skin, thereby treating a lack of skin elasticity. In yet some embodiments, a method of treating skin roughness comprises the step of administering to an individual suffering from skin roughness a composition disclosed herein, wherein the administration of the composition decreases skin roughness, thereby treating skin roughness. In still some embodiments, a method of treating a lack of skin tautness comprises the step of administering to an individual suffering from a lack of skin tautness a composition disclosed herein, wherein the administration of the composition makes the skin tauter, thereby treating a lack of skin tautness.

In some embodiments, a method of treating a skin stretch line or mark comprises the step of administering to an individual suffering from a skin stretch line or mark a composition disclosed herein, wherein the administration of the composition reduces or eliminates the skin stretch line or mark, thereby treating a skin stretch line or mark. In some embodiments, a method of treating skin paleness comprises the step of administering to an individual suffering from skin paleness a composition disclosed herein, wherein the administration of the composition increases skin tone or radiance, thereby treating skin paleness. In some embodiments, a method of treating skin wrinkles comprises the step of administering to an individual suffering from skin wrinkles a composition disclosed herein, wherein the administration of the composition reduces or eliminates skin wrinkles, thereby treating skin wrinkles. In yet some embodiments, a method of treating skin wrinkles comprises the step of administering to an individual a composition disclosed herein, wherein the administration of the composition makes the skin resistant to skin wrinkles, thereby treating skin wrinkles.

Aspects of the present specification provide, in part, administration of a composition disclosed herein wherein such administration promotes new collagen deposition. The compositions comprising a silk fibroin hydrogel component or particle and matrix polymer hydrogel component or particle support tissue ingrowth and new deposition of collagen (Example 21).

In an embodiment, administration of a composition comprising a silk fibroin hydrogel component and a matrix polymer hydrogel component as disclosed herein increases new collagen deposition. In some embodiments, administration of a composition comprising a silk fibroin hydrogel component and a matrix polymer hydrogel component as disclosed herein increases new collagen deposition by about 10%, about 20%, about 30%, about 40%, about 50%, about 60%, about 70%, about 80%, about 90%, or about 100%, relative to a the same or similar composition comprising the matrix polymer hydrogel component, but lacking the silk fibroin hydrogel component. In other some embodiments, administration of a composition comprising a silk fibroin hydrogel component and a matrix polymer hydrogel component as disclosed herein increases new collagen deposition by at least 25%, at least 50%, at least 75%, at least 100%, at least 125%, at least 150%, at least 175%, at least 200%, at least 225%, at least 250%, at least 275%, or at least 300%, relative to a the same or similar composition comprising the matrix polymer hydrogel component, but lacking the silk fibroin hydrogel component. In yet other some embodiments, administration of a composition comprising a silk fibroin hydrogel component and a matrix polymer hydrogel component as disclosed herein increases new collagen deposition by about 10% to about 100%, about 50% to about 150%, about 100% to about 200%, about 150% to about 250%, about 200% to about 300%, about 350% to about 450%, about 400% to about 500%, about 550% to about 650%, about 600% to about 700%, relative to a the same or similar composition comprising the matrix polymer hydrogel component, but lacking the silk fibroin hydrogel component.

As used herein, the terms "adipose tissue," "fat," "fat tissue", or "fatty tissue" include loose fibrous connective tissue comprising fat cells (adipocytes) and multiple types of regenerative cells, and may comprise brown and/or white adipose tissue taken from any body site, such as, e.g., subcutaneous, omental/visceral, interscapular, or mediastinal. It may be obtained from any organism having adipose tissue, or the adipose tissue used may be from a primary cell culture or an immortalized cell line.

Adipose tissue may be collected from the same individual who is undergoing the soft tissue replacement procedure (autograft), from a donor individual who is not the same individual as the one undergoing the soft tissue replacement procedure (allograft), or from an animal source (xenograft). As used herein, the term "autotransplantation" refers to the transplantation of organs, tissues, or cells from one part of the body to another part in the same individual, i.e., the donor and recipient are the same individual. Tissue transplanted by such "autologous" procedures is referred to as an autograft or autotransplant. As used herein, the term "allotransplantation" refers to the transplantation of organs, tissues, or cells from a donor to a recipient, where the donor and recipient are different individuals, but of the same species. Tissue transplanted by such "allologous" procedures is referred to as an allograft or allotransplant. As used herein, the term "xenotransplantation" refers to the transplantation of organs, tissues, or cells from a donor to a recipient, where the donor is of a different species as the recipient. Tissue transplanted by such "xenologous" procedures is referred to as a xenograft or xenotransplant.

Adipose tissue can be collected by any procedure that can harvest adipose tissue useful for the compositions and methods disclosed herein, including, without limitation a liposuction (lipoplasty) procedure or a lipectomy procedure. Procedures useful for collecting adipose tissue should minimize the trauma and manipulation associated with adipose tissue removed. Adipose tissue may be harvested from any suitable region, including, without limitation, a mammary region, an abdominal region, a thigh region, a flank region, a gluteal region, a trochanter region, or a gonadal region. Procedures useful for collecting adipose tissue are well known to a person of ordinary skill in the art. The selected procedures may be performed concomitantly with liposculpture.

A liposuction procedure harvests adipose tissue by aspirating the tissue using a cannula. The cannula may be connected to a syringe for manual aspiration or to a power assisted suction device, like an aspirator, adapted to collect the adipose tissue into a vacuum bottle. A liposuction procedure does not maintain an intact blood supply of the harvested tissue. The syringe may be a 10, 20 or 60 mL syringe fitted with a 12 or 14 gauge cannula. Non-limiting examples of liposuction procedures include suction-assisted liposuction (SAL), ultrasound-assisted liposuction (UAL), power-assisted liposuction (PAL), twin-cannula (assisted) liposuction (TCAL or TCL), or external ultrasound-assisted liposuction (XUAL or EUAL), or water-assisted liposuction (WAL). In addition, the liposuction procedures listed above can be used with any of the following procedures that vary the amount of fluid injected during the procedure, such as, e.g., dry liposuction, wet liposuction, super-wet liposuction, tumescent liposuction, or laser-assisted liposuction. An autologous soft tissue transfer procedure typically uses adipose tissue collected from a liposuction procedure.

Although the harvested tissue may be used directly to make the disclosed compositions, it is more typically processed to purify and/or enrich for healthy adipocytes and regenerative cells. For example, the harvested adipose tissue may be separated from any debris and/or contaminants such as, e.g., blood, serum, proteases, lipases, lipids and other oils, and/or other bodily fluids; tumescent fluid and/or other materials used in the liposuction procedure; and/or other impurities suctioned during the procedure. Methods useful in separating debris and/or contaminants from adipose tissue useful to make the disclosed compositions, including, without limitation, centrifugation, sedimentation, filtration, and/or absorption. In addition, or alternatively, the harvested adipose tissue may be processed by washing is a physiological buffer like saline to remove any debris and/or contaminants.

A lipectomy procedure harvests adipose tissue by surgical excision from a donor site in a manner that minimizes damage to the blood supply of the tissue using standard surgical operative procedures. This harvested tissue is then implanted into the region needing the soft tissue replacement. A tissue flap or tissue graft procedure typically uses adipose tissue collected from a lipectomy procedure. A tissue flap is a section of living tissue that maintained its blood supply as the tissue is moved from one area of the body to another.

A local flap uses a piece of skin and underlying tissue that lie adjacent to the wound, including adipose tissue. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. As an example, the transverse rectus abdominus myocutaneous) flap (TRAM flap) is a tissue flap procedure that uses muscle, fat and skin from an abdomen to create a new breast mound after a mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is a patch of healthy skin that is taken from one area of the body, called the "donor site," and used to cover another area where skin is missing or damaged. There are three basic types of skin grafts. A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are desired. As its name implies, a full-thickness (all layers) section of skin from the donor site are lifted. A composite graft is used when the wound to be covered needs more underlying support, as with skin cancer on the nose. A composite graft requires lifting all the layers of skin, adipose tissue, and sometimes the underlying cartilage from the donor site.

The amount of adipose tissue collected will typically vary from individual to individual and can depend on a number of factors including, but not limited to, amount of adipose tissue required for the soft tissue replacement method, aesthetic expectations, age, body habitus, coagulation profile, hemodynamic stability, co-morbidities, and physician preference. A liposuction procedure may harvest from about 1 mL to about 1500 mL of adipose tissue. A lipectomy procedure typically harvests about 1 g to about 5,000 g.

Adipose tissue comprises multiple types of regenerative cells. As used herein, the term "regenerative cell" refers to any cells that cause or contribute to complete or partial regeneration, restoration, or substitution of structure or function of an organ, tissue, or physiologic unit or system to thereby provide a therapeutic, structural or cosmetic benefit. Examples of regenerative cells include stem cells, progenitor cells, and precursor cells.

As used herein, the term "stem cell" refers to a multipotent regenerative cell with the potential to differentiate into a variety of other cell types that perform one or more specific functions and has the ability to self-renew. Some of the stem cells disclosed herein may be pluripotent. Exemplary examples of stem cells include, without limitation, adipose-derived stem cells (ASCs; adipose-derived stromal cells), endothelial-derived stem cells (ESCs), hemopoietic stem cells (HSCs), and mesenchyma stem cells (MSCs). Examples of differentiation include angiogenesis, neovascularization, adipogenesis and collagenesis As used herein, the term "progenitor cell" refers to an oligopotent regenerative cell with the potential to differentiate into more than one cell type, or a unipotent regenerative cell with the potential to differentiate into only a single cell type, that perform(s) one or more specific functions and has limited or no ability to self-renew. Exemplary examples of progenitor cells include, without limitation, endothelial progenitor cells, keratinocytes, monoblasts, myoblasts, and pericytes.

As used herein, the term "precursor cell" refers to a unipotent regenerative cell with the potential to differentiate into one cell type that performs one or more specific functions and may retain extensive proliferative capacity that enables the cells to proliferate under appropriate conditions. Exemplary examples of precursor cells include, without limitation, adipoblast (lipoblast or preadipocytes), de-differentiated adipocytes, angioblasts, endothelial precursor cells, fibroblasts, lymphoblasts, and macrophages.

A hydrogel composition disclosed herein may enhance differentiation of the multiple regenerative cells from the adipose tissue. In one embodiment, a hydrogel composition disclosed herein enhances differentiation of the multiple regenerative cells from the adipose tissue as compared to adipose tissue alone. In some embodiments, a hydrogel composition disclosed herein enhances differentiation of the multiple regenerative cells from the adipose tissue by at least about 50% at least about 100%, at least about 150%, at least about 200%, at least 250%, at least about 300%, at least about 350%, at least about 400%, at least about 450%, at least about 500%, at least about 750%, or at least about 1000% as compared to adipose tissue alone. In some embodiments, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue alone.

In another embodiment, a hydrogel composition disclosed herein enhances differentiation of the multiple regenerative cells from the adipose tissue as compared to adipose tissue with a hydrogel composition that is substantially identical except that the hyaluronic acid component and the silk fibroin component are not crosslinked. In some embodiments, a hydrogel composition disclosed herein enhances differentiation of the multiple regenerative cells from the adipose tissue by at least about 50% at least about 100%, at least about 150%, at least about 200%, at least about 250%, at least about 300%, at least about 350%, at least about 400%, at least about 450%, at least about 500%, at least about 750%, or at least about 1000% as compared to adipose tissue with a hydrogel composition that is substantially identical except that the hyaluronic acid component and the silk fibroin component are not crosslinked. In some embodiments, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the hyaluronic acid component and the silk fibroin component are not crosslinked. In some embodiments, a hydrogel composition that is substantially identical to a hydrogel composition disclosed herein except that the hyaluronic acid component and the silk fibroin component are not cross-linked comprises hyaluronic acid at a concentration of about 16 mg/mL or about 24 mg/mL and water.

In yet another embodiment, a hydrogel composition disclosed herein enhances differentiation of the multiple regenerative cells from the adipose tissue as compared to adipose tissue with a hydrogel composition that is substantially identical except that the silk fibroin component is absent. In some embodiments, a hydrogel composition disclosed herein enhances differentiation of the multiple regenerative cells from the adipose tissue by at least about 50% at least about 100%, at least about 150%, at least about 200%, at least 250%, at least about 300%, at least about 350%, at least about 400%, at least about 450%, at least about 500%, at least about 750%, or at least about 1000% as compared to adipose tissue with a hydrogel composition that is substantially identical except that the silk fibroin component is absent. In some embodiments, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the silk fibroin component is absent. In some embodiments, a hydrogel composition that is substantially identical to a hydrogel composition disclosed herein except that the silk fibroin component is absent comprises hyaluronic acid at a concentration of about 16 mg/mL or about 24 mg/mL and water.

Harvested adipose tissue useful in compositions of some embodiments can be supplemented with regenerative cells such as, e.g., stem cells, progenitor cells, and precursor cells. Regenerative cells may promote new blood vessel formation, diminish necrosis, and/or promote a supportive microenvironment in the transplanted tissue, thereby improving survivability of the transplanted tissue. Regenerative cells can be obtained from a variety of sources. For example, adipose tissue is rich in regenerative cells that have the ability to restore and reconstruct various soft tissue defects in response to local differentiation clues from the recipient site. As such, a portion of the collected adipose tissue may be further processed in order to purify regenerative cells that can then be added back to the remainder of the harvested adipose tissue in order to enrich this material for these cells. Exemplary methods describing such cell enrichment procedures can be found in, e.g., Hedrick and Fraser, Methods of Using Adipose Tissue-Derived Cells in Augmenting Autologous Fat Transfer, U.S. Patent Publication 2005/0025755, Yoshimura, et al., Characterization of Freshly Isolated and Cultured Cells Derived form the Fatty and Fluid Portions of liposuction Aspirates, J. Cell. Physiol. 208: 1011-1041 (2006); Yoshimura, et al., Cell-Assisted Lipotransfer for Facial Lipoatrophy: Effects of Clinical Use of Adipose-Derived Stem Cells, Dermatol. Surg. 34: 1178-1185 (2008); Yoshimura, et al., Cell-Assisted Lipotransfer for Cosmetic Breast Augmentation: Supportive Use of Adipose-Derived Stem/Stromal Cells, Aesth. Plast. Surg. 32: 48-55 (2008); each of which is hereby incorporated by reference in its entirety.

In addition, harvested adipose tissue can be supplemented with regenerative cells obtained from cell cultures, such as, e.g., primary cell cultures and established cell cultures. For example, a portion of harvested adipose tissue from an individual can be cultured in a manner to produce primary cell cultures enriched for regenerative cells. Alternatively, established cell lines derived from regenerative cells from adipose tissue, or another tissue source, can be cultured, harvested, and added to adipose tissue collected form an individual. Exemplary methods describing such cell culture compositions and procedures can be found in, e.g., Casteilla, et al., Method for Culturing Cells Derived from the Adipose Tissue and Uses Thereof, U.S. Patent Publication 2009/0246182; Chazenbalk, et al, Methods of Producing Preadipocytes and Increasing the Proliferation of Adult Adipose Stem/Progenitor Cells, U.S. Patent Publication 2009/0317367; Kleinsek and Soto, Augmentation and Repair of Sphincter Defects with Cells Including Adipocytic Cells, U.S. Patent Publication 2008/0299213; Rehman, et al., Secretion of Angiogenic and Antiapoptotic Factors by Human Adipose Stromal Cells, Circulation 109: r52-r58 (2004); Kilroy, et al., Cytokine Profile of Human Adipose-Derived Stem Cells: Expression of Angiogenic, Hematopoietic, and Pro-Inflammatory Factors, J. Cell. Physiol. 212: 702-709 (2007); each of which is hereby incorporated by reference in its entirety.

Harvested adipose tissue may be immediately used to make the compositions disclosed herein. Alternatively, harvested adipose tissue, whether unprocessed or processed, may be stored for used at some future date. Harvested tissue is typically stored using a slow freezing method of the tissue to −20° C., with or without cryopreservatives. Stored adipose tissue can typically be stored for at least 6 months.

In some embodiments, a hydrogel composition as described herein may include a hyaluronic acid: silk fibroin weight ratio of 17 to 4. The concentrations of hyaluronic acid can be from about 2 mg/mL to about 25 mg/mL and the silk fibroin can be from about 0.5 mg/mL to about 12 mg/mL. Further, the hydrogel composition may be used for fat grafting applications as an additive. The hydrogels can be formed with an EDC crosslinker and NHS as an activating agent.

Hydrogel compositions described herein can further have a storage modulus (G') and a loss modulus (G") each independently between about 500 Pa and about 4,000 Pa.

A general method of making hydrogel compositions as described herein can be achieved as follows. First, lyophilized hyaluronic acid fibers can be added to a concentrated (e.g., hydrated) silk fibroin solution. The pH can then be managed by the addition of one or more buffer salt and/or the addition of a base (e.g., NaOH). After the pH has been managed, the mixture can be hydrated and thoroughly mixed followed by addition of crosslinking agents. The crosslinking agents can be solids (e.g., powder). The hyaluronic acid and silk fibroin can be left to react. Once reacted, the resultant gel can be particle sized through a filter mesh (e.g., 100 μm) and can be dialyzed with buffer to purify (e.g., against any unused or unreacted crosslinker). The gel can then be sterilized (e.g., using isopropanol). This sterilization can also occur prior to purification. Once sterilized the gel may be ready for administration. The sterilized gel can also be further mixed within adipose tissue (e.g., human).

The sterilized gel either mixed with adipose tissue or not mixed with adipose tissue can be administered as described herein to treat a condition of, for example, the face, breast, hands, etc.

EXAMPLES

The methods and compositions of the present disclosure are further described in the following examples.

Example 1: Preparation of a Water-Soluble Silk Fibroin Solution

A 9.3 M LiBr solution was prepared by slowly dissolving 77.54 g of LiBr in 76.28 mL of MilliQ water. The LiBr solution was kept at 60° C. 24 g of sericin extracted knitted silkworm silk yarn was slowly submerged in the LiBr solution. The LiBr and silk solution was incubated in an oven at 60° C. for 6 hours. The solution was then loaded into a dialysis cassette MWCO 3.5 KDa and dialyzed against MilliQ water in a 4 L beaker at room temperature for 72 hours, changing the water at 1 hour, 4 hours, 12 hours and then twice a day.

Example 2: 80% HA-20% Silk Fibroin Crosslinked Gel Made Using EDC Chemistry and HMDA 1.2 mL of a 7 wt % Silk Fibroin (SF) MilliQ water solution and 20 mg of the diamine cross linker HMDA.2HCl was added to 13.8 mL of MilliQ water. 336 mg of high molecular weight hyaluronic acid (HA) was added to the solution. The mixture was allowed to hydrate for 60 minutes and homogenized by passing 30 times syringe-to-syringe. 576 mg of MES buffer was mixed with 321.6 mg of EDC and 72.9 mg of sulfoNHS in 5 mL MilliQ water. The reagent solution was mixed to the HA/SF solution by passing between syringes 30 times. The mixture was transferred to glass vials and left to react overnight at 4° C. The gel was sized using a 100 um mesh and centrifuged at 4000 rpm for 5 minutes. The sized gel was transferred to a cellulose ester membrane dialysis tubing MWCO 20 KDa and dialyzed against 1×PBS for 8 days at room temperature, changing the buffer twice a day. After dialysis, the gel was sized using a 60 um mesh, dispensed in 1 ml COC syringes, centrifuged at 5000 RPM for 5 min, and moist heat sterilized for 5 minutes at 128° C.

Example 3: 80% HA-20% SF Gel Cross Linked Using BDDE 2.4 mL of a 7 wt % Silk Fibroin (SF) MilliQ water solution and 1.25 mL of 1N NaOH MilliQ water solution were added to 1.35 mL MilliQ water. 494 mg of HMW HA was added to the SF/NaOH solution and allowed to hydrate for 60 minutes and homogenized by passing 30 times syringe-to-syringe. 85 mg of BDDE was added to the mixture and passed between syringes 30 times. The mixture was cured in a water bath at 50° C. for 2 hours. The gel was neutralized by adding 135 μL of 37% HCl and 4.86 mL PBS and passed between syringes 30 times. 7.5 mL of PBS was added to the gel and the gel was allowed to swell overnight at 4° C. The final HA/SF concentration of the gel was about 5 wt %. The gel was sized using a 100 um mesh and centrifuged at 4000 rpm for 5 minutes. The sized gel was transferred to a cellulose ester membrane dialysis tubing MWCO 20 KDa and dialyzed against 1×PBS for 8 days at 4° C., changing the buffer twice a day. After dialysis, the gel was dispensed in 1 ml COC syringes, centrifuged at 5000 RPM for 5 min, and sterilized with moist steam for 5 minutes at 128° C.

Example 4: Synthesis of Hyaluronic Acid—B. Mori Silk Fibroin Hydrogels with 5% Silk Fibroin Content The following procedure was used to produce hydrogels with a 20:1 (5%) HA-silk fibroin composition. 24.4 mg lysine methyl ester (LME) was dissolved in 14.54 mL MilliQ water. 0.46 mL of a 7% silk fibroin MilliQ water solution was dispersed in the solution. 393.3 mg hyaluronic acid, 2 MDa molecular weight, was added and left to hydrate for 1 hour. The solution was homogenized by syringe-tosyringe mixing. 576.0 mg 2-[morpholino]ethanesulfonic acid, 321.6 mg 1-ethyl-3-(3-dimethylaminopropyl) carbodiimide and 72.9 mg N-hydroxysulfosuccinimide were added to 5 mL MilliQ water and mixed to the hyaluronic acid/silk fibroin/lysine methyl ester solution by syringe-to-syringe mixing. The solution was transferred to a glass vial and centrifuged for 5 min at 4000 RPM to remove air bubbles. The resulting gel was allowed to react for 16 hrs at 4 aC. The gel was then particulated through a 60 micron pore-sized mesh. Following sizing, the gel was dialyzed in PBS pH7.4 for 6 days through a 20 kDa molecular-weight cut-off cellulose ester membrane at 4° C. The gel was then dispensed into 1 mL syringes, centrifuged at 4000 rpm for 10 minutes to eliminate any non-absorbed water and sterilized by autoclaving in wet steam at 128° C. for 5 minutes.

Example 5: Synthesis of Hyaluronic Acid—B. Mori Silk Fibroin Hydrogels with 20% Silk Fibroin Content The following procedure was used to produce hydrogels with a 17:4 (20%) HA-silk fibroin composition. 24.4 mg lysine methyl ester (LME) was dissolved in 13.8 mL MilliQ water. 336.0 mg hyaluronic acid, 2 MOa molecular weight, was added and left to hydrate for 1 hour. The solution was homogenized by syringe-to-syringe mixing. 1.2 mL of a 7% silk fibroin MilliQ water solution was mixed to the hyaluronic acid using a static mixer. 576.0 mg 2-[morpholino]ethanesulfonic acid, 321.6 mg 1-ethyl-3-(3-dimethylaminopropyl) carbodiimide and 72.9 mg N-hydroxysulfosuccinimide were added to 5 mL MilliQ water and mixed to the hyaluronic acid/silk fibroin solution using the static mixer. The solution was transferred to a glass vial and centrifuged for 5 min at 4000 RPM to remove air bubbles. The resulting gel was allowed to react for 16 hrs at 4° C. The gel was then particulated through a 60 micron pore-sized mesh. Following sizing, the gel was dialyzed in PBS pH7.4 for 6 days through a 20 kOa molecular-weight cut-off cellulose ester membrane at 4° C. The gel was then dispensed into 1 mL syringes, centrifuged at 4000 rpm for 10 minutes to eliminate any non-absorbed water and sterilized by autoclaving in wet steam at 128° C. for 5 minutes.

Example 6: Rheological Characterization of Hyaluronic Acid—B. Mori Silk Fibroin Hydrogels Oscillatory parallel plate rheology was used to characterize the mechanical properties of the hydrogels synthesized in Example 4 and Example 5 using an Anton Paar MCR 301. A plate diameter of 25 mm was used at a gap height of 1 mm. A frequency sweep from 0.1 to 10 Hz at a fixed strain of 2% with logarithmic increase in frequency was applied followed by a strain sweep between 0.1% and 300% at a fixed frequency of 5 Hz with logarithmic increase in strain. The storage modulus (G') and loss modulus (G") were recorded from frequency sweep measurements at 5 Hz. Values from measurements of samples from Examples 4 and 5 are presented in Table 1.

TABLE 1

Rheological properties of hyaluronic acid-silk fibroin (HA-Fbn) hydrogels

| Sample ID | [HA] (mg/mL) | [Fbn] (mg/mL) | G' (Pa) | G" (Pa) |
|---|---|---|---|---|
| HA-Fbn 20:1 | 20 | 1 | 1170 | 31.7 |
| HA-Fbn 17:4 | 17 | 4 | 1250 | 47.3 |

TABLE 1-continued

Rheological properties of hyaluronic acid-silk fibroin (HA-Fbn) hydrogels

| Sample ID | [HA] (mg/mL) | [Fbn] (mg/mL) | G' (Pa) | G" (Pa) |
|---|---|---|---|---|
| HA-Fbn 17:4 (A) | 17 | 4 | 1030 | 40.0 |
| HA-Fbn 17:4 (B) | 17 | 4 | 867 | 31.6 |
| HA-Fbn 17:4 (C) | 17 | 4 | 1200 | 53.7 |
| HA-Fbn 17:4 (D) | 17 | 4 | 1010 | 41.9 |

Example 7: Swelling Ratios of Hyaluronic Acid—B. Mori Silk Fibroin Hydrogels Swelling ratios were determined using thermogravimetric analysis (TGA) on HA-silk fibroin (A), (B) and (D) hydrogels synthesized in Example 5. The solid content variation in the gels was calculated after equilibration with phosphate buffer. For each gel, approximately 1 mL was dispensed into a 15 mL Falcon tube, followed by addition of 10 mL of phosphate buffered saline, pH 7.4. The gels were thoroughly mixed with the buffer and vortexed for 30 seconds. The gels were then allowed to equilibrate in the buffer for 24 hrs at room temperature. After this time, the suspensions were centrifuged at 4000 RPM in a swinging bucket rotor for 5 minutes. The supernatant buffer was then decanted and the gels were dispensed into 1 mL syringes, centrifuged at 4000 rpm for 10 minutes to eliminate any non-absorbed water. The TGA measurements were performed in triplicates. The swelling ratio was determined by dividing the final solid content of the swollen gel by the solid content feed, i.e., hyaluronic acid, silk fibroin and crosslinker. The swelling results of samples from Example 5 are presented in Table 2. A swelling ratio less than 1 indicates that the gel lost water upon equilibration and centrifugation.

TABLE 2

Swelling ratios of hyaluronic acid-silk fibroin hydrogels

| Sample ID | [HA] (mg/mL) | [Fbn] (mg/mL) | Average Swelling Ratio |
|---|---|---|---|
| HA-Fbn 17:4 (A) | 17 | 4 | 1.38 |
| HA-Fbn 17:4 (B) | 17 | 4 | 1.59 |
| HA-Fbn 17:4 (D) | 17 | 4 | 1.83 |

Example 8: Biocompatibility of Hyaluronic Acid—B Mori Silk Fibroin Hydrogels Biocompatibility was tested on HA-silk fibroin 20:1 (Example 4) and HA-silk fibroin 17:4 (Example 5). Results were compared to Juvederm™ XP (Allergan), an injectable dermal filler comprised of a cross-linked hyaluronic acid, and Star-HA hydrogel, which contain only hyaluronic acid and multi-epoxy crosslinkers. These gels are known to cause low to moderate inflammation in vivo. Male 14-weeks old Sprague-Dawley rats were administered 50 μL of hydrogel using a 27 gauge needle. Injections were placed intradermally on the dorsum of each animal under anesthesia with four injections per rat. After one week, the gels were explanted. Sections were cut around each implant in its entirety, including the surrounding tissue defined by a radius of approximately 1 cm. CD68 staining assay to assess the degree of CD68 macrophage marker were performed on the explanted gels for histology. CD68 scores were determined for each of the gels, and are presented in Table 3 below. All average scores were below 3, which indicates low to moderate inflammation. The results obtained for HA-silk fibroin hydrogels were statistically identical to Star HA. Thus, the HA-silk fibroin hydrogels show low levels of inflammation, indicating biocompatibility.

TABLE 3

Biocompatibility CD68 scores of hyaluronic acid-silk fibroin (HA-Fbn) hydrogels

| Sample | Crosslinker | [HA] (mg/mL) | [Fbn] (mg/mL) | Average Score |
|---|---|---|---|---|
| Juvederm XP | BDDE | 24 | 0 | 0.83 ± 0.61 |
| Star HA | PEG-epoxide | 26 | 0 | 2.50 ± 1.10 |
| HA-Fbn 20:1 | LME | 20 | 1 | 1.92 ± 0.63 |
| HA-Fbn 17:4 | LME | 17 | 4 | 2.99 ± 0.74 |

Example 9: Attachment of Human Adipose Derived Stem Cell (hASC) on Hyaluronic Acid—*B. Mori* Silk Fibroin Hydrogels The HA-silk fibroin 20:1 (Example 4) and 17:4 (Example 5) hydrogels were tested for hASC attachment. 100 µL gel beds were made in a non-TCP (tissue culture polystyrene) 48-well plate and hASC having a concentration of $6 \times 10^4$ hASC/mL were placed on top of the gel beds. Cells were cultured overnight at 37° C. The next day, cells were stained with Calcein AM for 30 min. and viewed with an inverted fluorescent microscope. Microscope focus was set on the bottom of the wells and was moved up to locate the attached cells. The results were compared to hASC attachment to a TPC plate. An examination of the micrographs showed the cells attached to both samples, but showed a significant spreading (rather than concentrated) on the HA-Fbn 17:4 hydrogel, indicating the positive effect of fibroin on cell attachment to the hydrogel, as well as the effect of the concentration of fibroin in the hydrogel on cell attachment.

Example 10: Support of hASC Viability on Hyaluronic Acid—*B. Mori* Silk Fibroin Hydrogels Samples of HA-Fbn hydrogels 17:4 from Example 5 were tested for their ability to support human adipose derived stem cell (hASC) viability. In 96-well plates, 50 µL gel beds were created in triplicate from the hydrogels of Example 5. Culture-expanded ASCs (Invitrogen) were plated at 10,000 cells/well on the gel beds in MesenPro RS medium with growth supplement (Invitrogen, CA). The cells were cultured for 18 hrs at 37° C., 5% $CO_2$, after which the XTT assay (American Type Culture Collection, VA) was performed. The 2,3-Bis-(2-methoxy-4-nitro-5-sulfophenyl)-2H-tetrazolium-5-carbonxanilide salt (XTT) is added to the wells and the cells are incubated. XTT is a colorless compound and when reduced by metabolically active cells it becomes a bright orange substance. The formazan product of XTT reduction is soluble so the absorbance can be read using a spectrophotometer at 475 nm and at 660 nm for non-specific readings. Cells adhered to the gels and exhibited a spread morphology. The viability of hASCs increased with increasing total biopolymer and collagen concentrations. Viability relative to tissue culture polystyrene (TCP) are shown in Table 4. Results are statistically similar, although the average result is slightly higher for some of the HA-Fbn hydrogels.

TABLE 4

ASC viability on hyaluronic acid-silk fibroin (HA-Fbn) hydrogels

| Sample | [HA] (mg/mL) | [Fbn] (mg/mL) | Viability (relative to TCP) |
|---|---|---|---|
| HA-Fbn 17:4 (A) | 17 | 4 | 52% |
| HA-Fbn 17:4 (B) | 17 | 4 | 55% |
| HA-Fbn 17:4 (C) | 17 | 4 | 81% |
| HA-Fbn 17:4 (D) | 17 | 4 | 57% |

Example 11: Support of hASC Proliferation on Hyaluronic Acid—*B. Mori* Silk Fibroin (HA-Fbn) Hydrogels Samples of HA-Fbn from Example 5 were tested for their ability to support ASC proliferation. In 96-well plates, 50 µL gel beds were created in triplicate from the HA-Fbn hydrogels. The hASCs (Invitrogen) were plated at 6,000 cells/well on the gel beds in MesenPro RS medium with growth supplement (Invitrogen). The hASCs were cultured for 3 days at 37° C., 5% $CO_2$, and proliferation was determined by XTT assay. Proliferation rates at day 3, relative to TCP. Results are shown in Table 5 and are statistically similar, although the average result is lightly higher for some of the HA-Fbn hydrogels.

TABLE 5 hASC proliferation (3-day) on hyaluronic acid-silk fibroin (HA-Fbn) hydrogels

| Sample | [HA] (mg/mL) | [Fbn] (mg/mL) | Proliferation (%) (relative to TCP) |
|---|---|---|---|
| HA-Fbn 17:4 (A) | 17 | 4 | 29 |
| HA-Fbn 17:4 (B) | 17 | 4 | 46 |
| HA-Fbn 17:4 (C) | 17 | 4 | 74 |
| HA-Fbn 17:4 (D) | 17 | 4 | 42 |

Example 12: Enhanced Diffusion of Adipose Tissue-Specific and Pro-Angiogenic Growth Factors in Hyaluronic Acid—*B. Mori* Silk Fibroin Hydrogels Two batches, HA-silk fibroin 17:4 (A) and (C) from Example 5 were assessed for their ability to allow diffusion of pro-angiogenic (vascular endothelial growth factor, VEGF) and adipose tissue-specific growth factors (adiponectin, leptin). Improved diffusion to any or all of these growth factors would support the enhanced survival of co-grafted tissue, especially fat, since nutrient diffusion may be important for sustained tissue viability. To do this, 100 µL of each hydrogel tested was loaded into a 8 µm transwell (24 well plate) in order to make a gel column. Known concentrations of target factors were loaded on top of the gel, diluted in fibroblast basal medium (Cat # PCS-201-030, ATCC). Plates were allowed to incubate at 37° C. with 5% $CO_2$ in a tissue culture incubator, for 60 hours, thereby allowing the factors to diffuse through the gels. Diffusion of the specified factors through each hydrogel was measured by ELISA (enzyme-linked immunosorbent assay) in the supernatant in the bottom chamber of the wells. Results are shown in Table 6 and indicate improved diffusion of VEGF and Adiponectin over the reference, Matrigel™ (Corning Life Sciences).

TABLE 6

Diffusion of growth factors and adipokines in hyaluronic acid-silk fibroin (HA-Fbn) hydrogels

| Sample | Adiponectin (%) | Leptin (%) | VEGF (%) |
|---|---|---|---|
| Matrigel | 19 | 44 | 30 |
| HA-Fbn 17:4 (A) | 82 | 18 | 79 |
| HA-Fbn 17:4 (B) | 74 | 18 | 71 |

Example 13: Enhanced Diffusion of Sugar Polymers and Proteins in Hyaluronic Acid—*B. Mori* Silk Fibroin (HA-Fbn) Hydrogels Hyaluronic acid silk fibroin (A) and (C) from Example 5 were assessed for their ability to allow diffusion of sugar polymers and proteins. Improved diffusion to any or all of these substances would support the enhanced survival of co-grafted tissue, especially fat, since nutrient diffusion is a critical element to sustained tissue viability. To do this, 100 μL of each hydrogel tested was loaded into a 8 μm transwell (24 well plate) in order to make a gel column. Known concentrations of target factors were loaded on top of the gel, diluted in fibroblast basal medium (Cat # PCS-201-030, ATCC). Plates were allowed to incubate at 37° C. with 5% $CO_2$ in a tissue culture incubator, for 60 hours, thereby allowing the factors to diffuse through the gels. Diffusion of the specified factors through each hydrogel was measured by ELISA using the supernatant in the bottom chamber of the wells. Diffusion was determined relative to no gel present. Results are shown in Table 7 and indicate improved levels of diffusion for FITC-dextran and total protein, compared to the positive control, Matrigel™.

TABLE 7

Diffusion of sugar polymers and proteins in hyaluronic acid-silk fibroin (HA-Fbn) hydrogels

| Sample | FITC-Dextran (%) | Total Protein (%) |
|---|---|---|
| Matrigel | 32 | 38 |
| HA-Fbn 17:4 (A) | 72 | 91 |
| HA-Fbn 17:4 (B) | 71 | 93 |

Example 14: Enhanced 3D Adipogenesis on Hyaluronic Acid—*B. Mori* Silk Fibroin (HA-Fbn) Hydrogels Hyaluronic acid-silk fibroin (A) from Example 5 was assessed for its ability to allow differentiation of hASCs to adipocytes. The physical and biological properties of the gel contribute to cell attachment, migration, and cell-cell and cell-matrix interactions, which dictate the differentiation of hASCs To evaluate the combined effects of these factors, a 3D culture was used for assessing adipogenesis capacity of HA-Fbn hydrogels. To do this, 500 μL of the hydrogel was loaded in to a 0.4 μm transwell (24 well plate) in order to make a gel column. The hASCs (Invitrogen) in 100 μL cell solution were plated at 1 million cells/well on the gel beds in Adipogenesis Media with Adipogenesis Differentiation Supplement (Invitrogen). Plates were allowed to incubate at 37° C. with 5% $CO_2$ in tissue culture incubator for 3 days, at which point the media was changed. At days 7, 14, 21, 28, and 35, media was collected and measured by ELISA using the supernatant in the bottom chamber of the wells. The secretion of adipose tissue-specific growth factors, such as diponectin, was assessed as an indication of adipocyte differentiation. The results are shown in Table 8 and show improved levels of adiponectin for HA-Fbn compared to the positive control HA-Collagen 12:6 (HA-CN 12:6).

TABLE 8

Adiponectin levels from differentiated adipocytes on hyaluronic acid-silk fibroin hydrogel

| Sample | Adiponectin [ng/mL] Day 21 | Adiponectin [ng/mL] Day 28 | Adiponectin [ng/mL] Day 35 |
|---|---|---|---|
| HA-CN 12:6 | 13 | 35 | 25 |
| HA-Fbn 17:4 (A) | 35 | 42 | 58 |

Example 15: In Vivo Volume Retention Studies of Hyaluronic Acid-Silk Fibroin (HA-Fbn) Hydrogels Three HA-Fbn hydrogels were prepared in a similar manner described to that of Examples 4 and 5 with HA:Fbn ratios of 19:2, 18:3, and 17:4. These hydrogels were mixed with human lipoaspirate at 2:1 lipo:gel ratio in a nude mouse model to assess the gels' ability to enhance fat graft viability and volume retention. Human lipoaspirate tissue was procured through means of ultrasound- or suction-assisted liposuction under informed consent, then consecutively centrifuged and washed 3× at 30 g for 5 min, in 1× phosphate buffered saline without cations (PBS, Invitrogen) inside a sterile biosafety cabinet. Next, 10 mL of washed lipoaspirate was transferred to a clean 100 mL sterile reservoir. To this tissue, 5 mL of sterile hydrogel was added and carefully blended by hand using a sterile spatula. The mixing procedure required 5 to 10 minutes of constant stirring with mechanical disruption of large pieces of tissue to generate a homogenous mixture. Then 1 mL syringes were filled with lipoaspirate/hydrogel until the plunger reached the 1 mL mark. The syringe was then capped with a sterile female leur-lok cap and maintained on ice blocks until use. Lipoaspirate/hydrogel mixes were implanted as 1 mL bolus subcutaneously on the dorsum of female 6-week-old nude mice under anesthesia with two injections per mouse. Each gel/lipo mixture was implanted through a small incision by 16 G cannula and the incision closed using surgical glue. A total of 14 injections of each material were made. Syringes were weighed before and after injection to determine the weight of injected material. After 6 weeks, the gels were harvested and weight and volume (using liquid displacement) were determined for each sample. A Lipo-only control sample was also tested. Samples were processed for histology by H&E staining.

FIG. 1 provides a graph of the volume retention over time of the three samples in comparison to the Lipo-only control. All of the tested HA-Fbn hydrogels have significantly higher volume than the Lipo-only control after 6 weeks. The HA-Fbn 17:4 shows significantly higher volume than the control. The volume retention for each of the samples and that of the Lipo-only control are provided in Table 9 below. It can be seen that the volume retention improved significantly over the Lipo-only control.

TABLE 9

Volume retention after 6 weeks for hyaluronic acid-silk fibroin hydrogel (HA-Fbn) fat grafts compared to a lipoaspirate-only control

| Sample | Average Retained Volume (%) | Improvement over Lipo-only control (%) |
| --- | --- | --- |
| Lipo only | 68.23 ± 9.63 | N/A |
| Lipo + HA-Fbn 19:2 | 90.57 ± 14.63 | 22.34 |
| Lipo + HA-Fbn 18:3 | 90.29 ± 18.06 | 22.06 |
| Lipo + HA-Fbn 17:4 | 90.93 ± 10.56 | 22.70 |

Figure 2A:
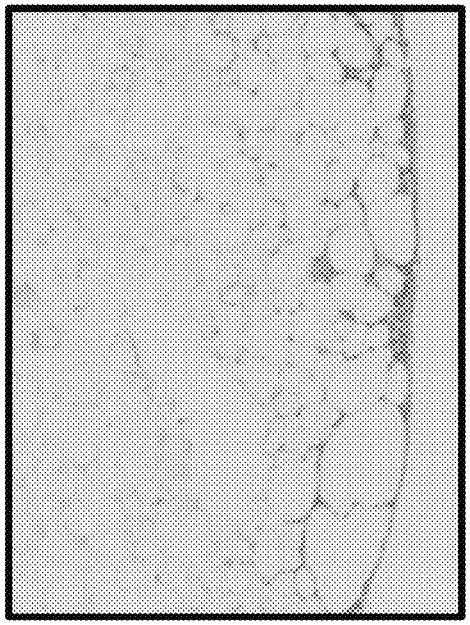
FIG. 2A provides a photograph of a tissue sample extracted after in vivo fat grafting of a composition consisting of only lipoaspirate.
Figure 2B:
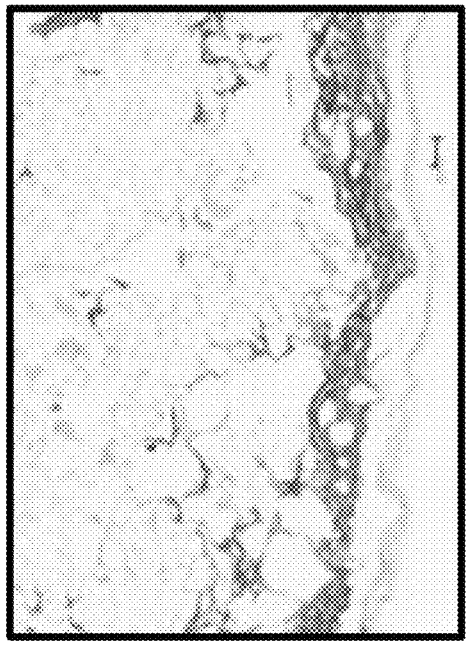
FIG. 2B provides a micrograph at 5× magnification of a tissue sample extracted and stained after in vivo fat grafting of a composition consisting of only lipoaspirate.
Figure 3A:
FIG. 3A provides a photograph of a tissue sample extracted after in vivo fat grafting of a hydrogel sample containing lipoaspirate in combination with a co-crosslinked HA-silk fibroin composition in a HA:silk fibroin ratio of 19:2.
Figure 3B:
FIG. 3B provides a micrograph at 5× magnification of a tissue sample extracted and stained after in vivo fat grafting of a hydrogel sample containing lipoaspirate in combination with a co-crosslinked HA-silk fibroin composition in a HA:silk fibroin ratio of 19:2.

FIG. 2A exhibits a photograph of the harvested Lipo-only control gel, and FIG. 3B provides a micrograph at 5× magnification of the H&E stained histological samples of the harvested Lipo-only control. The extracted Lipo-only control sample showed a lower amount of angiogenesis as indicated by the scant presence of darkened tissue in the photograph of FIG. 2A. Likewise, the micrograph of the Lipo-only sample shown in FIG. 2B shows little cell growth and angiogenesis. In this micrograph, it can be seen that most of the adipocytes in the Lipo-only sample are dead.

Figure 4B:
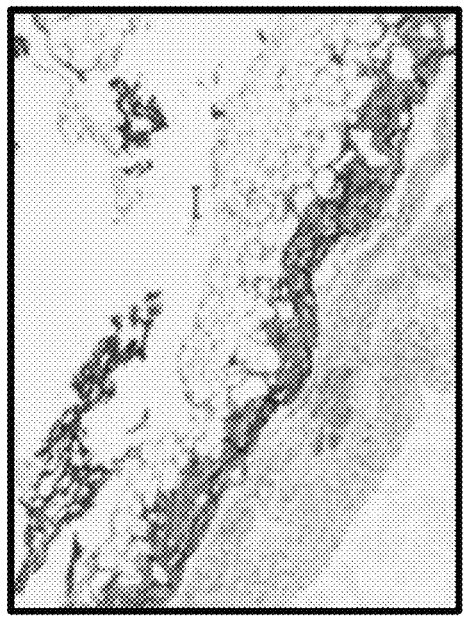
FIG. 4B provides a micrograph at 5× magnification of a tissue sample extracted and stained after in vivo fat grafting of a hydrogel sample containing lipoaspirate in combination with a co-crosslinked HA-silk fibroin composition in a HA:silk fibroin ratio of 18:3.
Figure 5B:
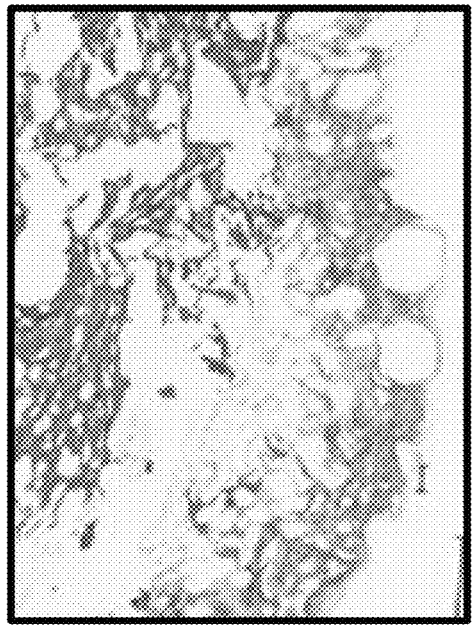
FIG. 5B provides a micrograph at 5× magnification of a tissue sample extracted and stained after in vivo fat grafting of a hydrogel sample containing lipoaspirate in combination with a co-crosslinked HA-silk fibroin composition in a HA:silk fibroin ratio of 17:4.
Figure 4A:
FIG. 4A provides a photograph of a tissue sample extracted after in vivo fat grafting of a hydrogel sample containing lipoaspirate in combination with a co-crosslinked HA-silk fibroin composition in a HA:silk fibroin ratio of 18:3.
Figure 5A:
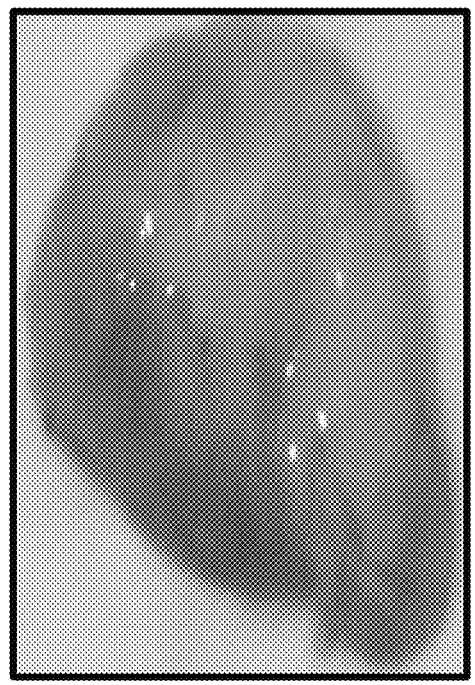
FIG. 5A provides a photograph of a tissue sample extracted after in vivo fat grafting of a hydrogel sample containing lipoaspirate in combination with a co-crosslinked HA-silk fibroin composition in a HA:silk fibroin ratio of 17:4.

In contrast, the photographs of the harvested HA-Fbn samples 19:2 (FIG. 3A), 18:3 (FIG. 4A), and 17:4 (FIG. 5A) all show an increase of darkened tissue areas, indicating a greater amount of angiogenesis than the Lipo-only control. In addition, the micrographs at 5× magnification of the H&E stained histological samples of the harvested HA-Fbn samples 19:2 (FIG. 3B), 18:3 (FIG. 4B), and 17:4 (FIG. 5B) show that these extracted samples contain more viable adipocytes than the Lipo-only control. Additionally, these samples all exhibit good cell infiltration and good angiogenesis, with low to moderate inflammation.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A soft tissue augmentation product comprising: a forming component comprising a hydrogel composition; wherein the hydrogel composition comprises water and a crosslinked macromolecular matrix, the crosslinked macromolecular matrix comprising: a hyaluronic acid component; and a silk fibroin component; wherein the hyaluronic acid component is crosslinked to the silk fibroin component by a multiamine cross linker; and wherein the soft tissue augmentation product is configured for administration to a soft tissue of a human subject.

Clause 2. The product of Clause 1, wherein the forming component comprises an injectable composition.

Clause 3. The product of any one of the preceding Clauses, wherein the forming component is configured for implantation into a human soft tissue.

Clause 4. The product of any one of the preceding Clauses, wherein the forming component further comprises human adipose tissue.

Clause 5. The product of Clause 4, wherein the human adipose tissue is autologous with the soft tissue.

Clause 6. The product of Clause 5, wherein the human adipose tissue comprises a lipoaspirate.

Clause 7. The product of any one of the preceding Clauses, further comprising a label comprising instructions to administer the forming component into a soft tissue.

Clause 8. The product of any one of the preceding Clauses, wherein the multiamine cross linker comprises a diamine cross linker.

Clause 9. The product of Clause 8, wherein the multiamine cross linker is selected from the group consisting of a hexamethylene diamine (HMDA), lysine, lysine methyl ester, and lysine ethyl ester.

Clause 10. The product of Clause 9, wherein the multiamine cross linker is lysine methyl ester.

Clause 11. The product of any one of the preceding Clauses, wherein the silk fibroin component comprises a B. mori silk fibroin.

Clause 12. The product of any one of the preceding Clauses, wherein the crosslinked macromolecular matrix has a weight ratio of the hyaluronic acid component to the silk fibroin component in the range of about 25:1 to about 1:1.

Clause 13. The product of Clause 12, wherein the crosslinked macromolecular matrix has a weight ratio of the hyaluronic acid component to the silk fibroin component of about 20:1.

Clause 14. The product of Clause 12, wherein the crosslinked macromolecular matrix has a weight ratio of the hyaluronic acid component to the silk fibroin component of about 17:4.

Clause 15. The product of Clause 12, wherein the crosslinked macromolecular matrix has a weight ratio of the hyaluronic acid component to the silk fibroin component of about 18:3.

Clause 16. The product of any one of the preceding Clauses, wherein the hyaluronic acid component is present in the hydrogel composition in a concentration of about 20 mg/mL to about 40 mg/mL, and wherein the silk fibroin component is present in the hydrogel composition in a concentration of about 0.1 mg/mL to about 20 mg/mL.

Clause 17. The product of Clause 16, wherein the hyaluronic acid component is present in the hydrogel composition in a concentration of about 9 mg/mL to about 32 mg/mL, and wherein the silk fibroin component is present in the hydrogel composition in a concentration of about 1 mg/mL to about 8 mg/mL.

Clause 18. The product of Clause 16, wherein the hyaluronic acid component is present in the hydrogel composition in a concentration of about 16 mg/mL to about 20 mg/mL, and wherein the silk fibroin component is present in the hydrogel composition in a concentration of about 2 mg/mL to about 5 mg/mL.

Clause 19. The product of Clause 16, wherein the hyaluronic acid component is present in the hydrogel composition in a concentration of about 17 mg/mL, and wherein the silk fibroin component is present in the hydrogel composition in a concentration of about 4 mg/mL.

Clause 20. The product of Clause 16, wherein the hyaluronic acid component is present in the hydrogel composition in a concentration of about 18 mg/mL, and wherein the silk fibroin component is present in the hydrogel composition in a concentration of about 3 mg/mL.

Clause 21. The product of Clause 16, wherein the hyaluronic acid component is present in the hydrogel composition in a concentration of about 19 mg/mL, and wherein the silk fibroin component is present in the hydrogel composition in a concentration of about 2 mg/mL.

Clause 22. The product of any one of the preceding Clauses, wherein the hyaluronic acid component has a molecular weight of about 1,000,000 daltons to about 5,000,000 daltons.

Clause 23. The product of any one of the preceding Clauses, wherein the hyaluronic acid component has a molecular weight of about 1,000,000 daltons to about 3,000,000 daltons.

Clause 24. A method of augmenting soft tissue of a human being comprising: providing a hydrogel composition comprising water and a crosslinked macromolecular matrix, the crosslinked macromolecular matrix comprising a hyaluronic acid component and a silk fibroin component, wherein the hyaluronic acid component is crosslinked to the silk fibroin component by a multiamine cross linker; and mixing the hydrogel composition with an ex vivo adipose tissue to produce a hydrogel-adipose tissue mixture.

Clause 25. The method of Clause 24, further comprising the step of introducing the hydrogel-adipose tissue mixture into a soft tissue of the human being.

Clause 26. The method of Clause 25, wherein the step of introducing comprises injecting the hydrogel-adipose tissue mixture into a soft tissue of the human being.

Clause 27. The method of Clause 25, wherein the step of introducing comprises configuring the hydrogel-adipose tissue mixture for implantation into a soft tissue of a human being and implanting the configured hydrogel-adipose tissue mixture into the soft tissue of the human being.

Clause 28. The method of any one of Clauses 24 to 27, wherein the adipose tissue comprises cells, the cells including adipocytes, multiple types of regenerative cells, stromal vascular fraction cells, or a combination thereof.

Clause 29. The method of any one of Clauses 24 to 28, wherein the adipose tissue is autologous with the soft tissue of the human being.

Clause 30. The method of Clause 29, wherein the adipose tissue comprises a lipoaspirate.

Clause 31. The method of any one of Clauses 24 to 30, wherein the multiamine cross linker comprises a diamine cross linker.

Clause 32. The method of Clause 31, wherein the multiamine cross linker is selected from the group consisting of a hexamethylene diamine (HMDA), lysine, lysine methyl ester, and lysine ethyl ester.

Clause 33. The method of Clause 32, wherein the multiamine cross linker comprises lysine methyl ester.

Clause 34 The method of any one of Clauses 24 to 33, wherein the silk fibroin component comprises a *B. mori* silk fibroin.

Clause 35. The method of any one of Clauses 24 to 34, wherein the crosslinked macromolecular matrix has a weight ratio of the hyaluronic acid component to the silk fibroin component in the range of about 25:1 to about 1:1.

Clause 36. The method of Clause 35, wherein the crosslinked macromolecular matrix has a weight ratio of the hyaluronic acid component to the silk fibroin component of about 20:1.

Clause 37. The method of Clause 35, wherein the crosslinked macromolecular matrix has a weight ratio of the hyaluronic acid component to the silk fibroin component of about 17:4.

Clause 38. The method of Clause 35, wherein the crosslinked macromolecular matrix has a weight ratio of the hyaluronic acid component to the silk fibroin component of about 18:3.

Clause 39. The method of any one of Clauses 24 to 38, wherein the hyaluronic acid component is present in the hydrogel composition in a concentration of about 20 mg/mL to about 40 mg/mL, and wherein the silk fibroin component is present in the hydrogel composition in a concentration of about 0.1 mg/mL to about 20 mg/mL.

Clause 40. The method of Clause 39, wherein the hyaluronic acid component is present in the hydrogel composition in a concentration of about 9 mg/mL to about 32 mg/mL, and wherein the silk fibroin component is present in the hydrogel composition in a concentration of about 1 mg/mL to about 8 mg/mL.

Clause 41. The method of Clause 39, wherein the hyaluronic acid component is present in the hydrogel composition in a concentration of about 16 mg/mL to about 20 mg/mL, and wherein the silk fibroin component is present in the hydrogel composition in a concentration of about 2 mg/mL to about 5 mg/mL.

Clause 42. The method of Clause 39, wherein the hyaluronic acid component is present in the hydrogel composition in a concentration of about 17 mg/mL, and wherein the silk fibroin component is present in the hydrogel composition in a concentration of about 4 mg/mL.

Clause 43. The method of Clause 39, wherein the hyaluronic acid component is present in the hydrogel composition in a concentration of about 18 mg/mL, and wherein the silk fibroin component is present in the hydrogel composition in a concentration of about 3 mg/mL.

Clause 44. The method of Clause 39, wherein the hyaluronic acid component is present in the hydrogel composition in a concentration of about 19 mg/mL, and wherein the silk fibroin component is present in the hydrogel composition in a concentration of about 2 mg/mL.

Clause 45. The method of any one of Clauses 24 to 44, wherein the hyaluronic acid component has a molecular weight of about 1,000,000 daltons to about 5,000,000 daltons.

Clause 46. The method of any one of Clauses 24 to 44, wherein the hyaluronic acid component has a molecular weight of about 1,000,000 daltons to about 3,000,000 daltons.

Clause 47. A method of grafting fat in a human subject, the method comprising providing a composition, wherein the composition comprises: (i) a hydrogel comprising: water and a crosslinked macromolecular matrix, the crosslinked macromolecular matrix comprising a hyaluronic acid component and a silk fibroin component, wherein the hyaluronic acid component is crosslinked to the silk fibroin component by a multiamine cross linker; and (ii) a fat component, comprising adipose tissue, adipocytes, or both.

Clause 48. The method of Clause 47, wherein the fat component has been explanted from the human subject.

Clause 49. The method of Clause 48, wherein the fat component comprises a lipoaspirate.

Clause 50. The method of any one of Clauses 47 to 49, further comprising the step of administering the composition to soft tissue of the human subject, thereby increasing the volume of fat in the soft tissue of the subject.

Clause 51. The method of Clause 50, wherein the step of administering the composition results in an increase in fat graft volume retention as compared to administering the fat component alone.

Clause 52. The method of any one of Clauses 50 to 51, wherein the administering comprises injecting or implanting the composition into the soft tissue of the human subject.

Clause 53. The method of any one of Clauses 47 to 52, wherein the composition has a fat component:hydrogel weight ratio of about 1:1 to about 5:1.

Clause 54. The method of any one of Clauses 47 to 53, wherein the multiamine cross linker comprises a diamine cross linker.

Clause 55. The method of Clause 54, wherein the multiamine cross linker is selected from the group consisting of a hexamethylene diamine (HMDA), lysine, lysine methyl ester, and lysine ethyl ester.

Clause 56. The method of Clause 55, wherein the multiamine cross linker is lysine methyl ester.

Clause 57. The method of any one of Clauses 47 to 56, wherein the silk fibroin is a *B. mori* silk fibroin.

Clause 58. The method of any one of Clauses 47 to 57, wherein the crosslinked macromolecular matrix has a weight ratio of hyaluronic acid to silk fibroin in the range of about 25:1 to about 1:1.

Clause 59. The method of Clause 58, wherein the crosslinked macromolecular matrix has a weight ratio of hyaluronic acid to silk fibroin of about 20:1.

Clause 60. The method of Clause 58, wherein the crosslinked macromolecular matrix has a weight ratio of hyaluronic acid to silk fibroin of about 17:4.

Clause 61. The method of Clause 58, wherein the crosslinked macromolecular matrix has a weight ratio of hyaluronic acid to silk fibroin of about 18:3.

Clause 62. The method of any one of Clauses 47 to 61, wherein the hyaluronic acid component is present in the hydrogel in a concentration of about 20 mg/mL to about 40 mg/mL, and wherein the silk fibroin component is present in the hydrogel in a concentration of about 0.1 mg/mL to about 20 mg/mL.

Clause 63. The method of Clause 62, wherein the hyaluronic acid component is present in the hydrogel in a concentration of about 9 mg/mL to about 32 mg/mL, and wherein the silk fibroin component is present in the hydrogel in a concentration of about 1 mg/mL to about 8 mg/mL.

Clause 64. The method of Clause 62, wherein the hyaluronic acid component is present in the hydrogel in a concentration of about 16 mg/mL to about 20 mg/mL, and the silk fibroin component is present in the hydrogel in a concentration of about 2 mg/mL to about 5 mg/mL.

Clause 65. The method of Clause 62, wherein the hyaluronic acid component is present in the hydrogel in a concentration of about 17 mg/mL, and wherein the silk fibroin component is present in the hydrogel in a concentration of about 4 mg/mL.

Clause 66. The method of Clause 62, wherein the hyaluronic acid component is present in the hydrogel in a concentration of about 18 mg/mL, and wherein the silk fibroin component is present in the hydrogel in a concentration of about 3 mg/mL.

Clause 67. The method of Clause 62, wherein the hyaluronic acid component is present in the hydrogel in a concentration of about 19 mg/mL, and wherein the silk fibroin component is present in the hydrogel in a concentration of about 2 mg/mL.

Clause 68. The method of any one of Clauses 47 to 67, wherein the hyaluronic acid component has a molecular weight of about 1,000,000 daltons to about 5,000,000 daltons.

Clause 69. The method of any one of Clauses 47 to 68, wherein the hyaluronic acid component has a molecular weight of about 1,000,000 daltons to about 3,000,000 daltons.

Clause 70. The method of any one of Clauses 47 to 69, wherein the fat component contains adipocytes, and wherein administering the composition enhances adipocyte proliferation as compared to administering adipocytes alone.

Clause 71. The method of any one of Clauses 47 to 69, wherein the fat component contains adipose tissue, and wherein administering the composition enhances adipose tissue growth as compared to administering adipose tissue alone.

Clause 72. A method of grafting fat in a soft tissue of a human subject, the method comprising: (i) injecting a hydrogel component into the soft tissue of the subject, wherein the hydrogel component comprises water and a crosslinked macromolecular matrix, the crosslinked macromolecular matrix comprising a hyaluronic acid component and a silk fibroin component, wherein the hyaluronic acid component is crosslinked to the silk fibroin component by a multiamine cross linker; and (ii) administering a fat component to the soft tissue of the subject, wherein the fat component contains adipose tissue, adipocytes, or both, and wherein the fat component has been explanted from the human subject; thereby increasing the volume of fat in the soft tissue of the human subject.

Clause 73. The method of Clause 72, wherein the injection of the hydrogel component and the administration of the fat component to the soft tissue is performed sequentially.

Clause 74. The method of Clause 73, wherein the injection of the hydrogel component to the soft tissue precedes the administration of the fat component to the soft tissue.

Clause 75. The method of any one of Clauses 72 to 74, wherein the fat component is injected into the soft tissue.

Clause 76. The method of Clause 72, wherein the hydrogel component is contacted with the fat component prior to the injection to provide a single composition, which is injected into the soft tissue of the human subject.

Clause 77. The method of Clause 76, wherein the composition has a fat component:hydrogel weight ratio of 1:1 to 5:1.

Clause 78. The method of any one of Clauses 72 to 77, wherein the multiamine cross linker comprises a diamine cross linker.

Clause 79. The method of Clause 78, wherein the multiamine cross linker is selected from the group consisting of a hexamethylene diamine (HMDA), lysine, lysine methyl ester, and lysine ethyl ester.

Clause 80. The method of Clause 79, wherein the multiamine cross linker is lysine methyl ester.

Clause 81. The method of any one of Clauses 72 to 81, wherein the silk fibroin is a *B. mori* silk fibroin.

Clause 82. The method of any one of Clauses 72 to 81, wherein the crosslinked macromolecular matrix has a weight ratio of the hyaluronic acid to the silk fibroin in the range of about 25:1 to about 1:1.

Clause 83. The method of Clause 82, wherein the crosslinked macromolecular matrix has a weight ratio of the hyaluronic acid to the silk fibroin of about 20:1.

Clause 84. The method of Clause 82, wherein the crosslinked macromolecular matrix has a weight ratio of the hyaluronic acid to the silk fibroin of about 17:4.

Clause 85. The method of Clause 82, wherein the crosslinked macromolecular matrix has a weight ratio of the hyaluronic acid to the silk fibroin of about 18:3.

Clause 86. The method of any one of Clauses 72 to 85, wherein the hyaluronic acid component is present in the hydrogel component in a concentration of about 20 mg/mL to about 40 mg/mL, and wherein the silk fibroin component is present in the hydrogel component in a concentration of about 0.1 mg/mL to about 20 mg/mL.

Clause 87. The method of Clause 86, wherein the hyaluronic acid component is present in the hydrogel component in a concentration of about 9 mg/mL to about 32 mg/mL, and wherein the silk fibroin component is present in the hydrogel component in a concentration of about 1 mg/mL to about 8 mg/mL.

Clause 88. The method of Clause 86, wherein the hyaluronic acid component is present in the hydrogel component in a concentration of about 16 mg/mL to about 20 mg/mL, and wherein the silk fibroin component is present in the hydrogel component in a concentration of about 2 mg/mL to about 5 mg/mL.

Clause 89. The method of Clause 86, wherein the hyaluronic acid component is present in the hydrogel component in a concentration of about 17 mg/mL, and wherein the silk fibroin component is present in the hydrogel component in a concentration of about 4 mg/mL.

Clause 90. The method of Clause 86, wherein the hyaluronic acid component is present in the hydrogel component in a concentration of about 18 mg/mL, and wherein the silk fibroin component is present in the hydrogel component in a concentration of about 3 mg/mL.

Clause 91. The method of Clause 86, wherein the hyaluronic acid component is present in the hydrogel component in a concentration of about 19 mg/mL, and wherein the silk fibroin is present in the hydrogel component in a concentration of about 2 mg/mL.

Clause 92. The method of any one of Clauses 72 to 91, wherein the hyaluronic acid component has a molecular weight of about 1,000,000 daltons to about 5,000,000 daltons.

Clause 93. The method of any one of Clauses 72 to 91, wherein the hyaluronic acid component has a molecular weight of about 1,000,000 daltons to about 3,000,000 daltons.

Clause 94. The method of any one of Clauses 72 to 93, wherein fat graft volume retention is increased as compared to administering the fat component alone.

Clause 95. The method of any one of Clauses 72 to 94, wherein adipocyte proliferation is enhanced as compared to administering adipocytes alone.

Clause 96. The method of any one of Clauses 72 to 95, wherein adipose tissue growth is enhanced as compared to administering adipose tissue alone.

Further Considerations

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a Clause may include some or all of the words (e.g., steps, operations, means or components) recited in a clause, a sentence, a phrase or a paragraph. In some embodiments, a Clause may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

As used herein, the terms "about," "substantially," and "approximately" may provide an industry-accepted tolerance for their corresponding terms and/or relativity between items, such as from less than one percent to five percent.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of improving an aesthetic quality of an anatomic feature of a subject, the method comprising administering a hydrogel composition comprising hyaluronic acid, silk fibroin, and an ex vivo tissue to the subject, wherein the hyaluronic acid is crosslinked to the silk fibroin by a water-soluble coupling agent.

2. The method of claim 1, wherein the hydrogel composition is injected into the anatomic feature of the subject.

3. The method of claim 1, wherein the hydrogel composition is implanted into the anatomic feature of the subject.

4. The method of claim 1, wherein the ex vivo tissue comprises adipose tissue or fat tissue.

5. The method of claim 1, wherein the ex vivo tissue comprises adipose-derived progenitor cells.

6. The method of claim 1, wherein the water-soluble coupling agent comprises a multiamine crosslinker.

7. The method of claim 1, wherein the hydrogel composition has a weight ratio of the hyaluronic acid to the silk fibroin in the range of about 25:1 to about 1:1.

8. The method of claim 1, wherein the hyaluronic acid is present in the hydrogel composition in a concentration of about 16 mg/mL to about 20 mg/mL, and wherein the silk fibroin is present in the hydrogel composition in a concentration of about 2 mg/mL to about 5 mg/mL.

9. A method of augmenting soft tissue of a human being comprising:
providing a hydrogel composition comprising hyaluronic acid and silk fibroin, wherein the hyaluronic acid is crosslinked to the silk fibroin by a water-soluble coupling agent; and
mixing the hydrogel composition with an ex vivo tissue to produce a hydrogel tissue mixture.

10. The method of claim 9, further comprising the step of introducing the hydrogel tissue mixture into a soft tissue of the human being.

11. The method of claim 9, wherein the water-soluble coupling agent comprises a multiamine crosslinker.

12. The method of claim 11, wherein the multiamine crosslinker comprises lysine methyl ester.

13. The method of claim 9, wherein the hydrogel composition has a weight ratio of the hyaluronic acid to the silk fibroin in the range of about 25:1 to about 1:1.

14. The method of claim 9, wherein the hyaluronic acid is present in the hydrogel composition in a concentration of about 16 mg/mL to about 20 mg/mL, and wherein the silk fibroin is present in the hydrogel composition in a concentration of about 2 mg/mL to about 5 mg/mL.

15. The method of claim 9, wherein the ex vivo tissue comprises adipose tissue or fat tissue.

16. The method of claim 9, wherein the ex vivo tissue comprises adipose-derived progenitor cells.

17. A method of treating a soft tissue condition of a subject, the method comprising:
administering a hydrogel composition to a site of the soft tissue condition of the subject, the hydrogel composition comprising hyaluronic acid and silk fibroin crosslinked by a water-soluble coupling agent and an ex vivo adipose tissue, wherein the administration of the hydrogel composition improves the soft tissue condition.

18. The method of claim 17, wherein a therapeutically effective amount of the hydrogel composition is administered.

19. The method of claim 17, wherein the hydrogel composition is administered in an amount of from about 0.01 mL to about 200 mL.

20. The method of claim 17, wherein the hydrogel composition is administered using a syringe with a needle or a catheter.

21. The method of claim 17, wherein the hydrogel composition is administered topically.

22. The method of claim 17, wherein the hydrogel composition is administered by direct surgical implantation.

23. The method of claim 17, wherein the hydrogel composition further comprises an anesthetic.

24. The method of claim 17, wherein the hydrogel composition has a storage modulus of about 1 Pa to about 10,000 Pa.

25. The method of claim 17, wherein the hydrogel composition has a loss modulus of about 1 Pa to about 500 Pa.

26. The method of claim 17, wherein the water-soluble coupling agent is a carbodiimide.

* * * * *